(12) United States Patent
Bedoe et al.

(10) Patent No.: US 12,186,522 B2
(45) Date of Patent: Jan. 7, 2025

(54) DISINFECTING CAP

(71) Applicant: Medline Industries, Inc., Northfield, IL (US)

(72) Inventors: Scott Bedoe, McHenry, IL (US); James Burgess, Lake Bluff, IL (US); Brent Skupien, Hawthorn Woods, IL (US); Christopher Dalton, Mundelein, IL (US); Pere Berkowitz, Highland Park, IL (US); David Noskowicz, Spring Grove, IL (US)

( * ) Notice: Subject to any disclaimer, the term of this patent is extended or adjusted under 35 U.S.C. 154(b) by 503 days.

(21) Appl. No.: 17/390,854

(22) Filed: Jul. 30, 2021

(65) Prior Publication Data

US 2021/0353927 A1    Nov. 18, 2021

Related U.S. Application Data

(63) Continuation of application No. 17/014,901, filed on Sep. 8, 2020, now Pat. No. 11,464,962, which is a
(Continued)

(51) Int. Cl.
*A61M 39/16* (2006.01)
*A61M 39/20* (2006.01)

(52) U.S. Cl.
CPC ............ *A61M 39/20* (2013.01); *A61M 39/16* (2013.01); *A61M 2205/0205* (2013.01)

(58) Field of Classification Search
CPC .......... A61M 2205/0205; A61M 39/16; A61M 39/162; A61M 39/165
See application file for complete search history.

(56) References Cited

U.S. PATENT DOCUMENTS

| 877,946 A | 2/1908 | Overton |
| 2,735,427 A | 2/1956 | Sullivan |

(Continued)

FOREIGN PATENT DOCUMENTS

| AU | 2001273300 B2 | 1/2002 |
| AU | 2012258435 A1 | 12/2012 |

(Continued)

OTHER PUBLICATIONS

China National Intellectual Property Administration Search Report; Application No. 201680060068.6; Medline Industries, Inc. (Bedoe, Scott, et al.); Sep. 17, 2021.

(Continued)

*Primary Examiner* — Deanna K Hall
(74) *Attorney, Agent, or Firm* — Robert D. Spendlove

(57) ABSTRACT

A device for cleaning medical implements is disclosed, in particular a device for cleaning vascular or other fluid access sites. The device includes a cap having an opening to receive an access site. The cap may be used in the following manner: A healthcare worker may, with gloved hands, open the cap packaging and place the cap over the port of a medical implement to be cleaned. The healthcare worker may wipe the site by either applying a turning motion or by simply pushing the cap onto the port. The cap could then remain secured in place by threads other mechanisms. A cap in place on a medical implement may be a positive indication that a desired site of the medical implement is clean. The cap may include a disinfecting substance.

17 Claims, 26 Drawing Sheets

Related U.S. Application Data continuation of application No. 15/240,301, filed on Aug. 18, 2016, now Pat. No. 10,828,484.

(60) Provisional application No. 62/216,650, filed on Sep. 10, 2015, provisional application No. 62/208,364, filed on Aug. 21, 2015, provisional application No. 62/208,213, filed on Aug. 21, 2015, provisional application No. 62/208,243, filed on Aug. 21, 2015.

(56) References Cited

U.S. PATENT DOCUMENTS

| | | | |
|---|---|---|---|
| 2,851,036 A | 9/1958 | Lipari | |
| 4,243,035 A | 1/1981 | Barrett | |
| 4,317,446 A | 3/1982 | Ambrosio et al. | |
| 4,335,756 A | 6/1982 | Sharp et al. | |
| 4,340,148 A | 7/1982 | Beckham | |
| 4,440,207 A | 4/1984 | Genatempo et al. | |
| 4,624,664 A | 11/1986 | Peluso et al. | |
| 4,799,926 A | 1/1989 | Haber | |
| 5,187,843 A | 2/1993 | Lynch | |
| 5,471,706 A | 12/1995 | Wallock et al. | |
| 5,694,978 A | 12/1997 | Heilmann et al. | |
| 5,820,604 A | 10/1998 | Fox et al. | |
| 5,827,244 A | 10/1998 | Boettger | |
| 5,941,857 A | 8/1999 | Nguyen et al. | |
| 5,989,229 A | 11/1999 | Chiappetta | |
| 6,045,539 A | 4/2000 | Menyhay | |
| 6,126,640 A | 10/2000 | Tucker et al. | |
| 6,152,913 A | 11/2000 | Feith et al. | |
| 6,419,825 B1 | 7/2002 | Hahmann et al. | |
| 6,592,564 B2 | 7/2003 | Finch et al. | |
| 6,679,870 B1 | 1/2004 | Finch et al. | |
| 6,685,694 B2 | 2/2004 | Finch et al. | |
| 7,282,186 B2 | 10/2007 | Lake, Jr. et al. | |
| D607,325 S | 1/2010 | Rogers et al. | |
| 7,763,006 B2 | 7/2010 | Tennican | |
| 7,780,794 B2 | 8/2010 | Rogers et al. | |
| 7,794,675 B2 | 9/2010 | Lynn | |
| 7,799,010 B2 | 9/2010 | Tennican | |
| 7,857,793 B2 | 12/2010 | Raulerson et al. | |
| 7,922,701 B2 | 4/2011 | Buchman | |
| 7,972,322 B2 | 7/2011 | Tennican | |
| 7,985,302 B2 | 7/2011 | Rogers et al. | |
| 8,065,773 B2 | 11/2011 | Vaillancourt et al. | |
| 8,069,523 B2 | 12/2011 | Vaillancourt et al. | |
| 8,083,729 B2 | 12/2011 | Colantonio et al. | |
| 8,162,899 B2 | 4/2012 | Tennican | |
| 8,167,847 B2 | 5/2012 | Anderson et al. | |
| 8,172,825 B2 | 5/2012 | Solomon et al. | |
| 8,177,761 B2 | 5/2012 | Howlett et al. | |
| 8,197,749 B2 | 6/2012 | Howlett et al. | |
| 8,206,514 B2 | 6/2012 | Rogers et al. | |
| 8,231,587 B2 | 7/2012 | Solomon et al. | |
| 8,231,602 B2 | 7/2012 | Anderson | |
| 8,252,247 B2 | 8/2012 | Ferlic | |
| 8,262,643 B2 | 9/2012 | Tennican | |
| 8,273,303 B2 | 9/2012 | Ferlic et al. | |
| 8,328,767 B2 | 12/2012 | Solomon et al. | |
| 8,336,151 B2 | 12/2012 | Kerr et al. | |
| 8,336,152 B2 | 12/2012 | Vaillancourt et al. | |
| 8,343,112 B2 | 1/2013 | Solomon et al. | |
| 8,361,408 B2 | 1/2013 | Lynn | |
| 8,388,894 B2 | 3/2013 | Colantonio et al. | |
| 8,419,713 B1 | 4/2013 | Solomon et al. | |
| 8,480,968 B2 | 7/2013 | Lynn | |
| 8,491,546 B2 | 7/2013 | Hoang et al. | |
| 8,523,830 B2 | 9/2013 | Solomon et al. | |
| 8,523,831 B2 | 9/2013 | Solomon et al. | |
| 8,641,681 B2 | 2/2014 | Solomon et al. | |
| 8,647,308 B2 | 2/2014 | Solomon et al. | |
| 8,647,326 B2 | 2/2014 | Solomon et al. | |
| 8,671,496 B2 | 3/2014 | Vaillancourt et al. | |
| 8,728,056 B2 | 5/2014 | Colantonio et al. | |
| 8,740,864 B2 | 6/2014 | Hoang et al. | |
| 8,777,504 B2 | 7/2014 | Shaw et al. | |
| 8,808,637 B2 | 8/2014 | Ferlic | |
| 8,828,327 B2 | 9/2014 | Colantonio et al. | |
| 8,832,894 B2 | 9/2014 | Rogers et al. | |
| 8,834,650 B2 | 9/2014 | Rogers et al. | |
| 8,845,593 B2 | 9/2014 | Anderson et al. | |
| 8,961,475 B2 | 2/2015 | Solomon et al. | |
| 8,968,268 B2 | 3/2015 | Anderson et al. | |
| 8,999,073 B2 | 4/2015 | Rogers et al. | |
| 9,039,989 B2 | 5/2015 | Liu et al. | |
| 9,079,692 B2 | 7/2015 | Solomon et al. | |
| 9,114,915 B2 | 8/2015 | Solomon et al. | |
| 9,186,707 B2 | 11/2015 | Vaillancourt et al. | |
| 9,192,449 B2 | 11/2015 | Kerr et al. | |
| 9,259,284 B2 | 2/2016 | Rogers et al. | |
| 9,259,535 B2 | 2/2016 | Anderson et al. | |
| 9,283,367 B2 | 3/2016 | Hoang et al. | |
| 9,283,368 B2 | 3/2016 | Hoang et al. | |
| 9,352,140 B2 | 5/2016 | Kerr et al. | |
| 9,440,062 B2 | 9/2016 | Adams et al. | |
| 9,492,574 B2 | 11/2016 | Rasooly et al. | |
| 9,533,136 B2 | 1/2017 | Midgette et al. | |
| 9,561,298 B2 | 2/2017 | Ferlic et al. | |
| 9,572,904 B2 | 2/2017 | Ferlic | |
| 9,592,375 B2 | 3/2017 | Tennican | |
| 9,700,676 B2 | 7/2017 | Anderson et al. | |
| 9,700,677 B2 | 7/2017 | Anderson et al. | |
| 9,700,710 B2 | 7/2017 | Anderson et al. | |
| 9,707,308 B2 | 7/2017 | Ferlic et al. | |
| 9,707,348 B2 | 7/2017 | Anderson et al. | |
| 9,707,349 B2 | 7/2017 | Anderson et al. | |
| 9,707,350 B2 | 7/2017 | Anderson et al. | |
| 9,737,664 B2 | 8/2017 | Gardner et al. | |
| 9,809,355 B2 | 11/2017 | Solomon et al. | |
| 9,867,975 B2 | 1/2018 | Gardner et al. | |
| 9,895,526 B2 | 2/2018 | Korogi et al. | |
| 9,907,617 B2 | 3/2018 | Rogers | |
| 9,943,676 B2 | 4/2018 | Tekeste | |
| 9,999,471 B2 | 6/2018 | Rogers et al. | |
| 10,016,587 B2 | 7/2018 | Gardner et al. | |
| 10,022,530 B2 | 7/2018 | Tekeste | |
| 10,029,087 B2 | 7/2018 | Daneluzzi | |
| 10,046,156 B2 * | 8/2018 | Gardner | A61M 39/20 |
| 10,099,048 B2 | 10/2018 | Chiu et al. | |
| D834,187 S | 11/2018 | Ryan | |
| 10,155,056 B2 | 12/2018 | Solomon et al. | |
| 10,159,828 B2 | 12/2018 | Hoang et al. | |
| 10,166,085 B2 | 1/2019 | Ready et al. | |
| 10,166,339 B2 * | 1/2019 | Solomon | A61M 39/162 |
| 10,166,381 B2 | 1/2019 | Gardner et al. | |
| 10,195,000 B2 | 2/2019 | Rogers et al. | |
| 10,300,176 B2 | 5/2019 | Woo et al. | |
| 10,328,207 B2 | 6/2019 | Anderson et al. | |
| 10,335,584 B2 | 7/2019 | Hoang et al. | |
| 10,335,585 B2 | 7/2019 | Hoang et al. | |
| 10,357,579 B2 | 7/2019 | Chiu et al. | |
| 10,391,294 B2 | 8/2019 | Drmanovic | |
| 10,406,343 B2 | 9/2019 | Hoang et al. | |
| 10,493,261 B2 | 12/2019 | Solomon et al. | |
| 10,576,173 B2 | 3/2020 | Chiu et al. | |
| 10,589,080 B2 | 3/2020 | Hitchcock et al. | |
| 10,610,676 B2 | 4/2020 | Drmanovic | |
| 10,695,550 B2 | 6/2020 | Gardner et al. | |
| 10,744,316 B2 | 8/2020 | Fangrow | |
| 10,806,919 B2 | 10/2020 | Gardner et al. | |
| 10,821,278 B2 | 11/2020 | Gardner | |
| 10,828,484 B2 | 11/2020 | Bedoe et al. | |
| 10,850,085 B2 | 12/2020 | Tekeste | |
| 11,331,464 B2 | 5/2022 | Hoang et al. | |
| 11,464,962 B2 | 10/2022 | Bedoe et al. | |
| 11,497,904 B2 | 11/2022 | Fangrow | |
| 2004/0028877 A1 | 2/2004 | Itoh et al. | |
| 2005/0013836 A1 | 1/2005 | Raad | |
| 2005/0147525 A1 | 7/2005 | Bousquet | |
| 2008/0033371 A1 | 2/2008 | Updegraff et al. | |
| 2008/0039803 A1 | 2/2008 | Lynn | |
| 2008/0235888 A1 | 10/2008 | Vaillancourt et al. | |
| 2009/0028750 A1 | 1/2009 | Ryan | |
| 2009/0099529 A1 | 4/2009 | Anderson et al. | |

(56) References Cited

U.S. PATENT DOCUMENTS

| | | |
|---|---|---|
| 2009/0137969 A1 | 5/2009 | Colantonio et al. |
| 2010/0003067 A1 | 1/2010 | Shaw et al. |
| 2010/0306938 A1 | 12/2010 | Rogers et al. |
| 2011/0064512 A1 | 3/2011 | Shaw |
| 2011/0232020 A1 | 9/2011 | Rogers et al. |
| 2011/0265825 A1 | 11/2011 | Rogers et al. |
| 2011/0296586 A1 | 12/2011 | Jaros |
| 2011/0314619 A1 | 12/2011 | Schweikert |
| 2012/0042466 A1 | 2/2012 | Colantonio et al. |
| 2012/0109073 A1 | 5/2012 | Anderson et al. |
| 2012/0216359 A1 | 8/2012 | Rogers et al. |
| 2012/0216360 A1 | 8/2012 | Rogers et al. |
| 2012/0245531 A9 | 9/2012 | Anderson et al. |
| 2012/0296284 A1 | 11/2012 | Anderson et al. |
| 2013/0006194 A1 | 1/2013 | Anderson et al. |
| 2013/0035667 A1 | 2/2013 | Anderson et al. |
| 2013/0171030 A1 | 7/2013 | Ferlic et al. |
| 2013/0178804 A1 | 7/2013 | Tennican |
| 2014/0135710 A1 | 5/2014 | Hoang et al. |
| 2014/0135711 A1 | 5/2014 | Hoang et al. |
| 2014/0155868 A1 | 6/2014 | Nelson et al. |
| 2014/0248182 A1 | 9/2014 | Solomon et al. |
| 2014/0261558 A1 | 9/2014 | Rogers et al. |
| 2014/0261581 A1 | 9/2014 | Rogers |
| 2014/0276449 A1 | 9/2014 | Charles et al. |
| 2014/0322075 A1 | 10/2014 | Ferlic et al. |
| 2014/0366914 A1 | 12/2014 | Kerr et al. |
| 2015/0000061 A1 | 1/2015 | Rogers et al. |
| 2015/0000062 A1 | 1/2015 | Rogers et al. |
| 2015/0018774 A1 | 1/2015 | Anderson et al. |
| 2015/0217106 A1 | 8/2015 | Banik et al. |
| 2016/0045629 A1 | 2/2016 | Gardner et al. |
| 2016/0101273 A1 | 4/2016 | Unger et al. |
| 2019/0209781 A1 | 7/2019 | Solomon et al. |
| 2019/0282796 A1 | 9/2019 | Hoang et al. |
| 2020/0121858 A1 | 4/2020 | Anderson et al. |
| 2020/0330741 A1 | 10/2020 | Fangrow |
| 2021/0001110 A1 | 1/2021 | Bedoe et al. |
| 2021/0046302 A1 | 2/2021 | Dombrowski et al. |
| 2021/0162194 A1 | 6/2021 | Gardner et al. |
| 2021/0170157 A1 | 6/2021 | Grant et al. |
| 2021/0353927 A1 | 11/2021 | Bedoe et al. |
| 2021/0353928 A1 | 11/2021 | Bedoe et al. |

FOREIGN PATENT DOCUMENTS

| | | |
|---|---|---|
| AU | 2013100345 A4 | 4/2013 |
| CA | 2692157 C | 5/2014 |
| CN | 101801435 A | 8/2010 |
| CN | 103191511 A | 7/2013 |
| EP | 2272431 A2 | 6/2010 |
| EP | 2606930 A1 | 6/2013 |
| EP | 2167166 B1 | 4/2020 |
| WO | 205188 A1 | 1/2002 |
| WO | 2009002474 A1 | 12/2008 |
| WO | 2013066285 A1 | 5/2013 |
| WO | 2017220729 A1 | 12/2017 |

OTHER PUBLICATIONS

International Search Report and Written Opinion of the International Searching Authority; International Patent Application No. PCT/US2022/049051; Medline Industries, LP; PUN, Yushek, et al.; dated Feb. 23, 2023.

Notification of Transmittal of the International Search Report and the Written Opinion of the International Searching Authority, or the Declaration, PCT/US2016/047863, Medline Industries, Inc. (Bedoe, Scott, et al.), Nov. 28, 2016.

\* cited by examiner

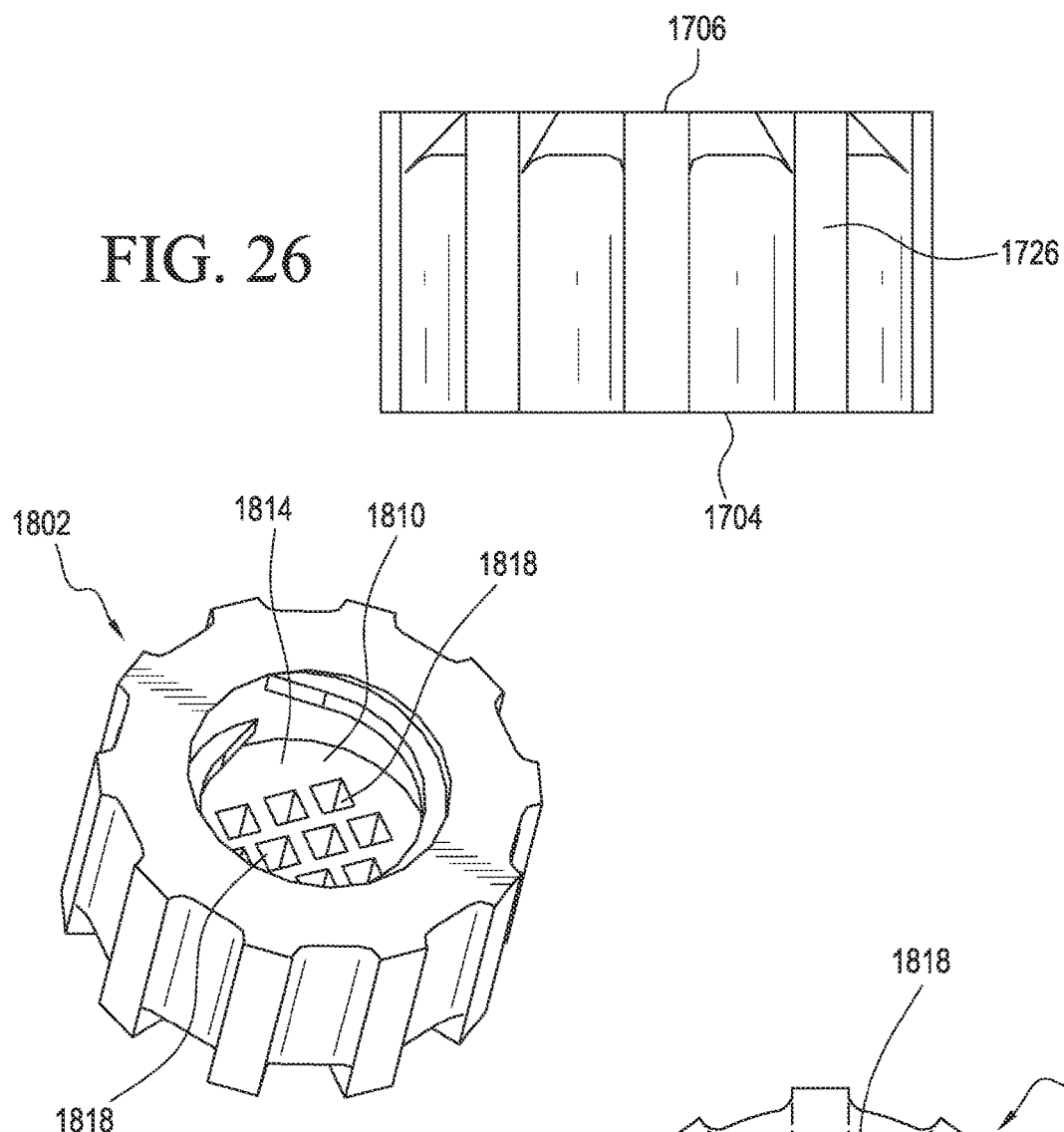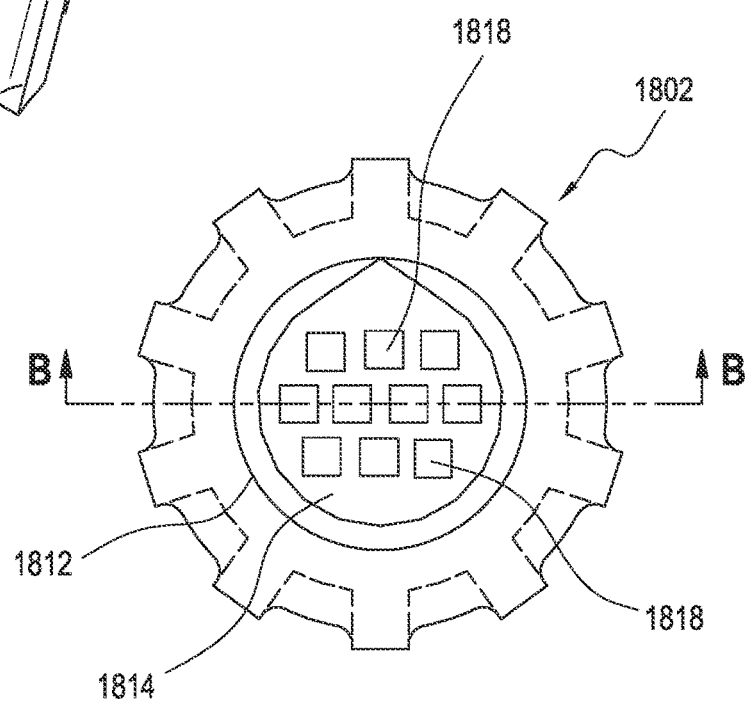

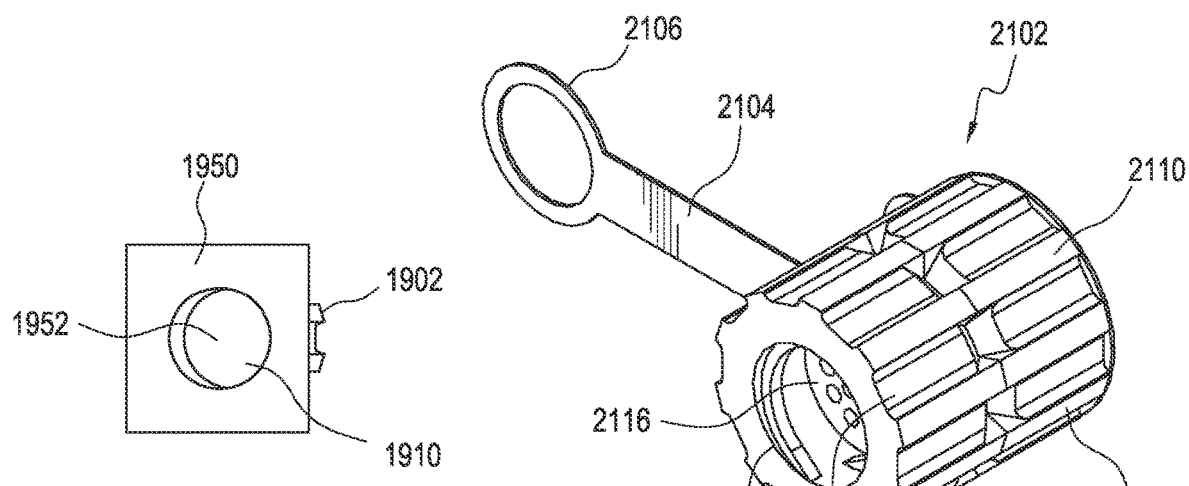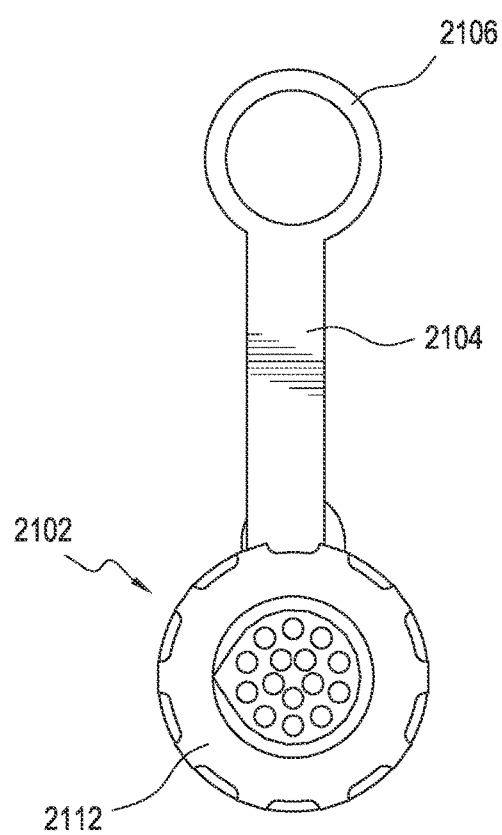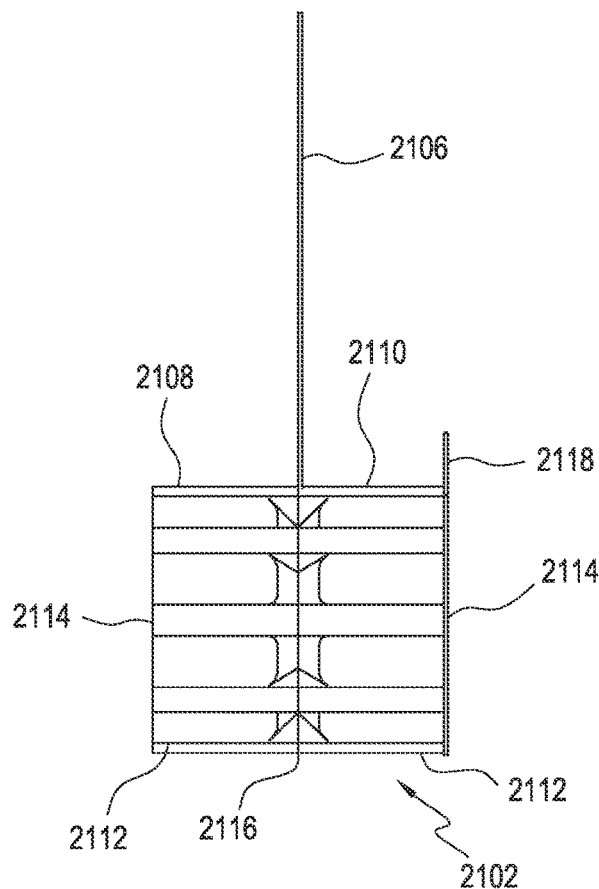
FIG. 36
FIG. 37
FIG. 38
FIG. 39

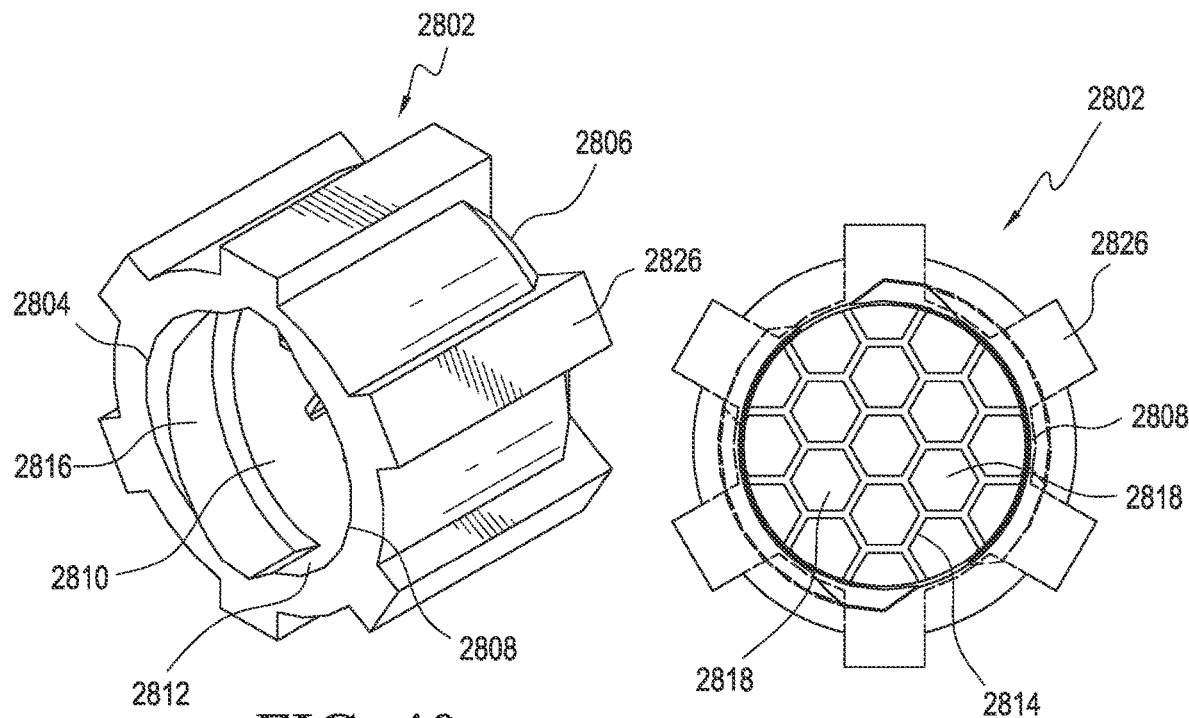
FIG. 40
FIG. 41
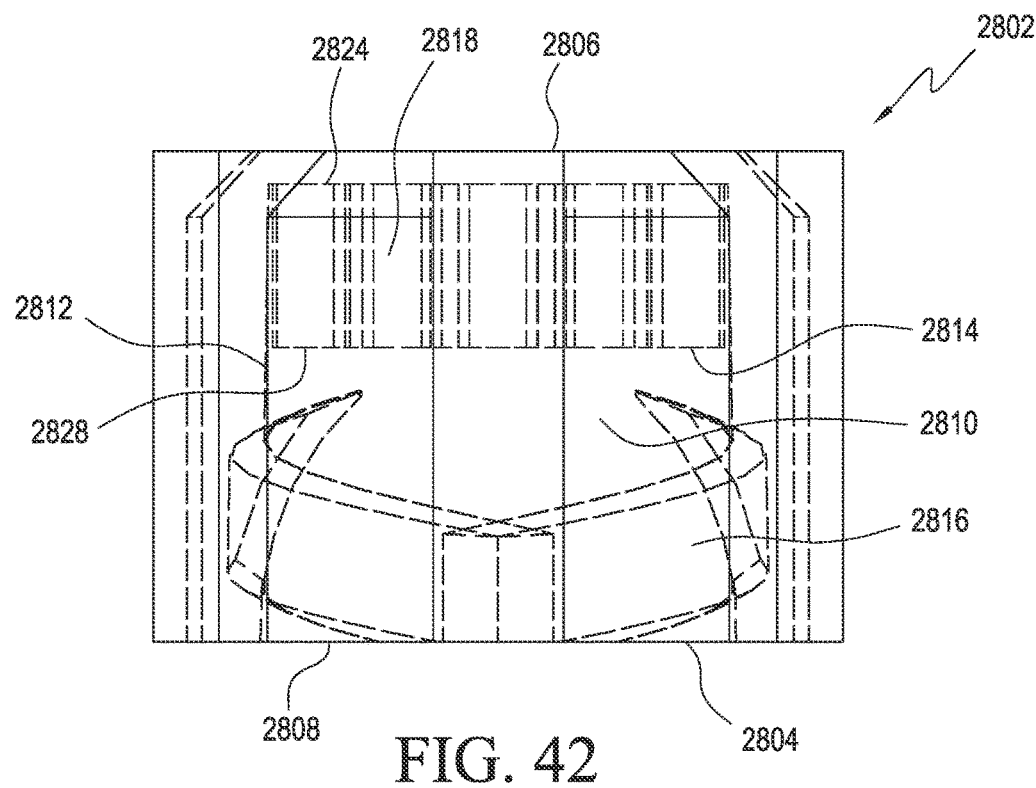
FIG. 42

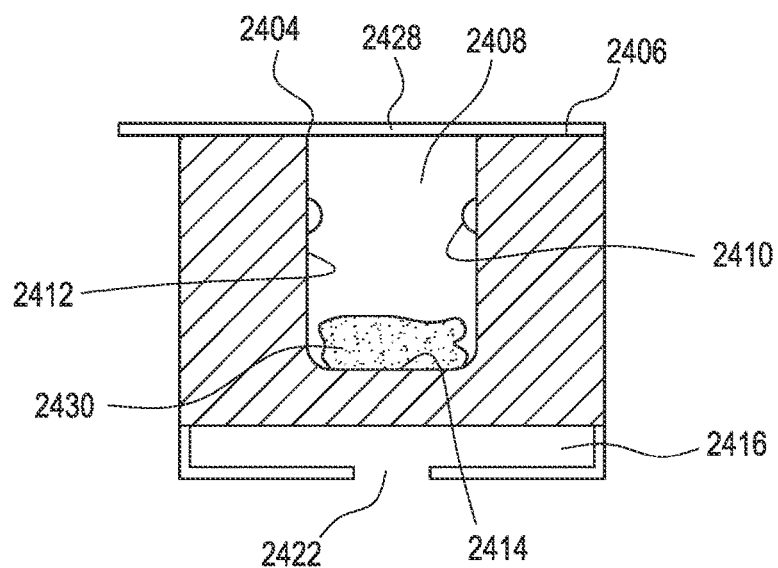
FIG. 45
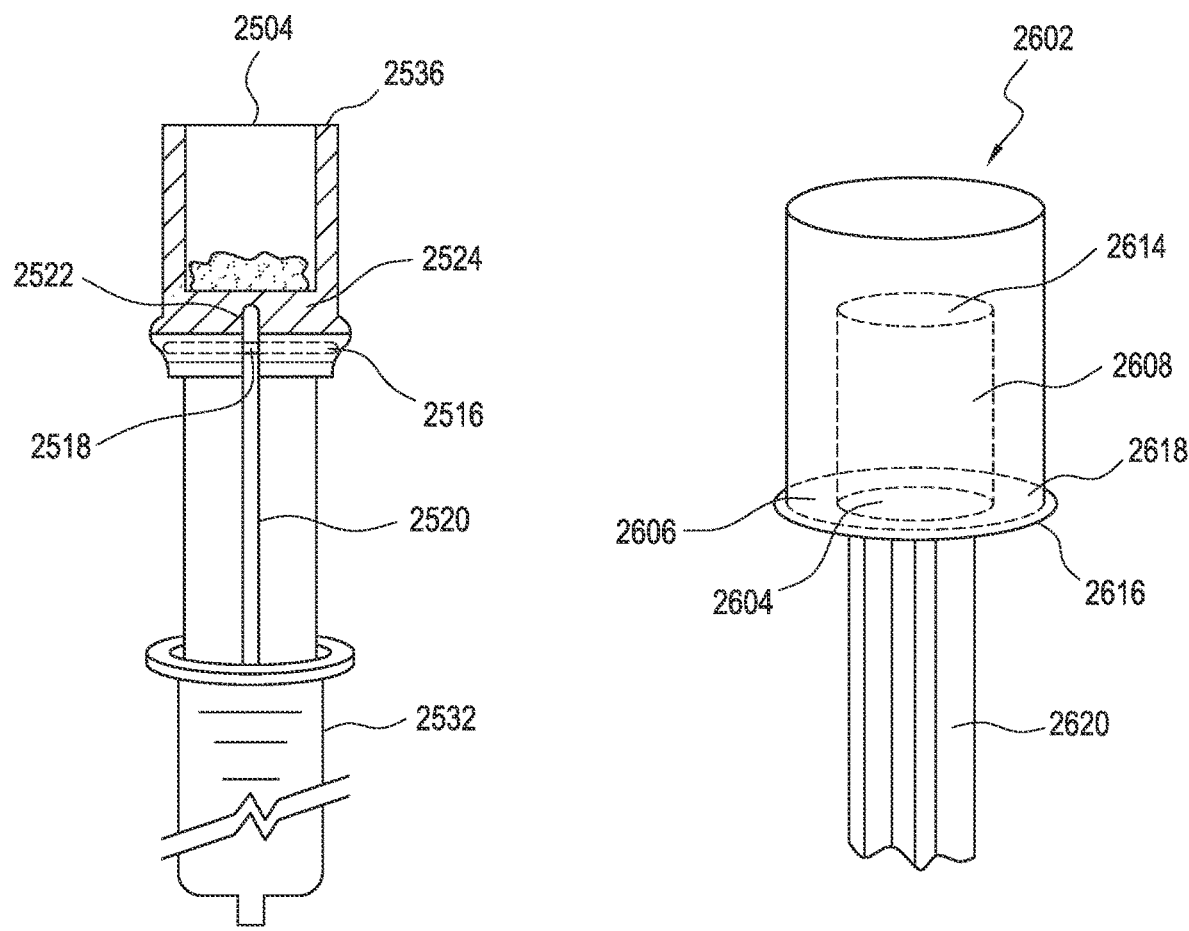
FIG. 46
FIG. 47

DISINFECTING CAP

RELATED APPLICATIONS

This is a continuation of U.S. patent application Ser. No. 17/014,901, entitled "Disinfecting Cap" and filed Sep. 8, 2020, which application is a continuation of U.S. patent application Ser. No. 15/240,301, entitled "Disinfecting Cap," filed Aug. 18, 2016, and issued on Nov. 10, 2020 as U.S. Pat. No. 10,828,484, which application claims priority to and the benefit of the following U.S. Provisional Application Nos.: 62/208,243, entitled "Disinfecting Cap" and filed Aug. 21, 2015; 62/208,364, entitled "Disinfecting Cap" and filed Aug. 21, 2015; 62/208,213, entitled "Disinfecting Cap with Valve" and filed Aug. 21, 2015; and 62/216,650, entitled "Disinfecting Cap with Fluid Reservoir" and filed Sep. 10, 2015. The contents of each of these applications are herein incorporated by reference in their entirety.

BACKGROUND

Within the medical field, and in particular the area of infusion of fluids or aspiration of fluids to or from a patient, there is a need to prevent the transmission of pathogens into or onto a patient from a potentially contaminated surface of a medical implement. Such pathogens include microorganisms such as bacteria and viruses. The transmission of pathogens into a patient may result in an infection that could be life threatening. Common sites for such transmissions are found at access "sites" of medical implements such as a luer port, vial, needle free valve, or an injection port of a vessel, tubing, or catheter. Even non-intrusive medical implements such as stethoscopes or otoscopes can transmit pathogens to a patient.

Accordingly, a need exists for an apparatus and technique for cleaning a site on a medical implement prior to contact with a patient.

BRIEF DESCRIPTION OF THE DRAWINGS

Advantages of the invention will become apparent upon reading the following detailed description and upon reference to the drawings.

FIG. 26 shows a side view of the cap of FIG. 22.

FIG. 27 shows a perspective view of disinfecting cap in accordance with embodiments of the invention.

FIG. 28 shows a view of the proximal end of the cap of FIG. 22.

FIG. 36 shows a perspective view of disinfecting cap in accordance with embodiments of the invention.

FIG. 37 shows a perspective view of disinfecting cap in accordance with embodiments of the invention.

FIG. 38 shows a top view of the disinfecting cap of FIG. 37.

FIG. 39 shows a side view of the disinfecting cap of FIG. 37.

FIG. 40 shows a perspective view of disinfecting cap in accordance with embodiments of the invention.

FIG. 41 shows a view of the proximal end of the cap of FIG. 40.

FIG. 42 shows a side view of the cap of FIG. 40.

FIG. 45 shows a cross-sectional view of the disinfecting cap of FIG. 43.

FIG. 46 shows a side view of disinfecting cap in accordance with embodiments of the invention.

FIG. 47 shows a perspective view of disinfecting cap in accordance with embodiments of the invention.

Figure 1:
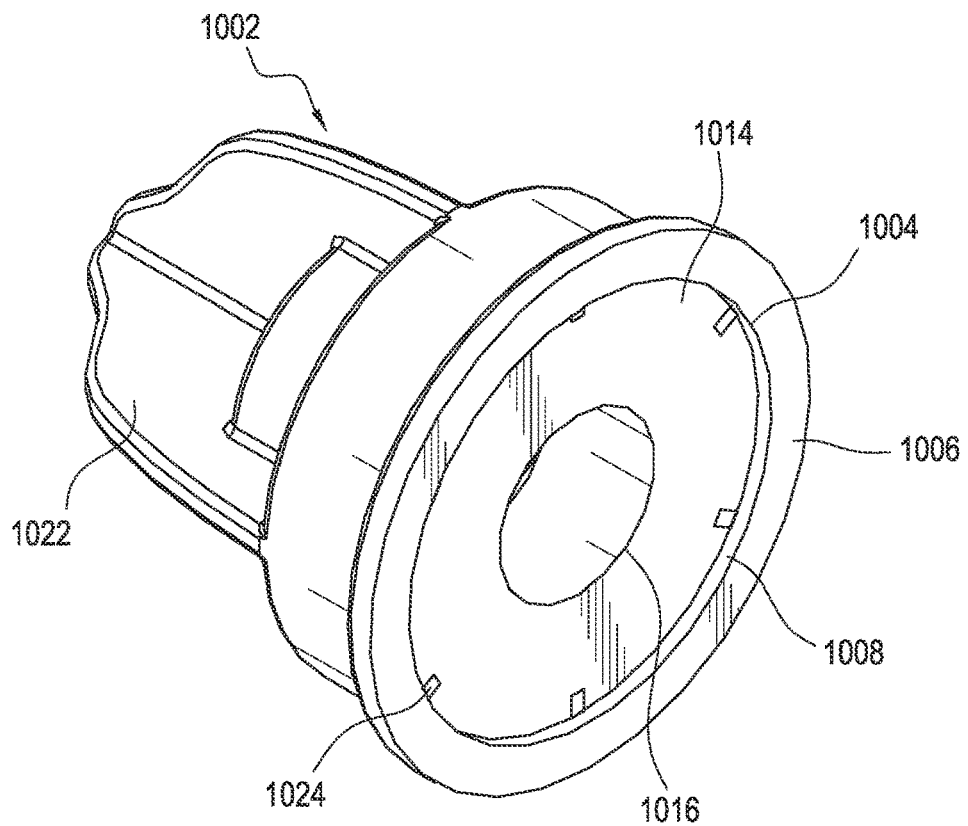
FIG. 1 shows a perspective view of disinfecting cap in accordance with embodiments of the invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, forward and rearward, and the like may be used solely to distinguish one entity or action from another entity or action without necessarily requiring or implying any actual such relationship, direction or order between such entities or actions.

The terms "proximal" and "distal" are used throughout this application when describing various embodiments. These terms are not intended to be limiting and are merely provided for ease of maintaining a consistent orientation when describing various embodiments. As used herein, proximal refers to the direction generally closer to the patient and/or medical device to be cleaned and distal refers to the direction generally farther from the patient and/or medical device to be cleaned.

This application provides a description of various implementations and embodiments of a device for cleaning medical implements, in particular a device for cleaning vascular or other fluid access sites. Various embodiments of the invention include a cap having an opening to receive an access site. Throughout this application illustrative embodiments refer to use of a cap to engage with a "port" as an example of such an access site. One of skill in the art would understand that the invention may also be used in conjunction with other access sites or other medical devices without access sites.

The following is a non-limiting example of how such a cap may be used by a healthcare worker: the healthcare worker may, with gloved hands, open the cap packaging and place the cap over the port of a medical implement to be cleaned. In certain embodiments, the healthcare worker may wipe the site by either applying a turning motion or by simply pushing the cap onto the port. The cap could then remain secured in place by threads other mechanisms described herein. A cap in place on a medical implement may be a positive indication that a desired site of the medical implement is clean. A vibrant color or other indicia may be used to allow instant visualization of a cap's presence from a door or hallway.

Embodiments of the cap described herein may include a disinfecting substance, such as a solution of a suitable microbiocide or germicide. The disinfecting substance can include an anti-bacterial disinfectant of any suitable type and suitable amount depending upon the size and structure of the cap. For example, in some embodiments the disinfecting substance may be an aqueous solution including about two percent (2%) chlorhexidine gluconate (chlorhexidine solution, "CHG"). In other embodiments, a solution including about 70 percent (70%) isopropyl alcohol ("IPA") in an aqueous solution is included in the disinfecting substance. In yet another embodiment, a solution including about 70 percent (70%) IPA and about two percent (2%) CHG in an aqueous solution is included in the disinfecting substance. In the latter solution, it is recognized that the concentration of IPA can vary from about 60 percent (60%) to about 90 percent (90%) and the concentration of CHG can vary from about one percent (1%) to about five percent (5%), in one embodiment.

Other suitable solution compositions and concentrations are also possible. For instance, povidone iodine, polyhexanide (polyhexamethylene biguanide, "PHMB"), benzalkonium chloride ("BAC"), chlorxylenol ("PCMX") or hydrogen peroxide solutions can be included in the disinfecting substance of further embodiments. Throughout this disclosure, reference to one or more of these disinfecting substances in relation to a cap embodiment should be understood to disclose the use of any other appropriate disinfecting substance as disclosed herein or as would be understood by one of ordinary skill in the art. In addition, embodiments of the disinfecting substance may be in a liquid or a gel form.

In various embodiments of the invention described herein, the port comes in contact with the disinfecting substance in liquid or gel form, or with an absorbent material infused with the disinfecting substance. However, it may not be necessary for the surface of the port to contact the liquid or gel disinfecting substance. For example, if IPA is used as part of a disinfecting solution, IPA vapors trapped within the cap may act as a disinfectant for the port without requiring contact between the liquid solution and the site being cleaned.

Various materials may be used to manufacture the cap embodiments described herein. Appropriate materials may include polyurethane ("PU"), polypropylene ("PP"), thermoplastic elastomer ("TPE"), thermoplastic vulcanizate ("TPV") such as Santoprene, or other materials as would be understood by one of ordinary skill in the art. Various embodiments described herein recite the use of particular materials, but one of ordinary skill would understand that other appropriate materials could be substituted for the disclosed material.

Various embodiments also describe the use of foam material. Such foam may be formed of polyurethane ("PU") or another appropriate absorbent material. Alternatively, other absorbent materials may be used in place of foam, including for example, a felted non-woven or other fibrous materials.

Figure 2:
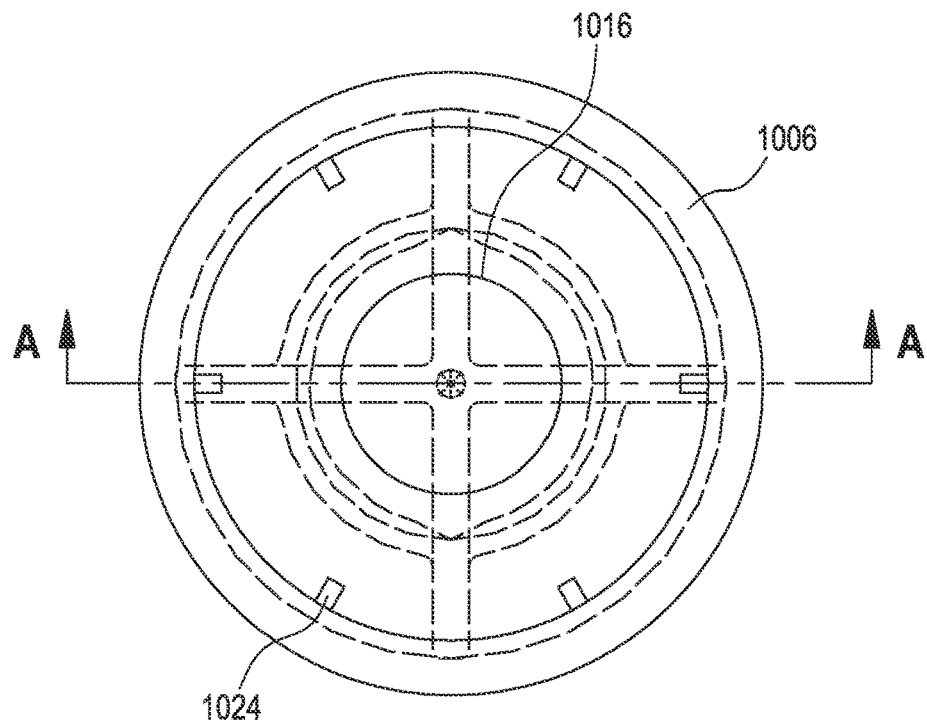
FIG. 2 shows an end view of the disinfecting cap of FIG. 1.
Figure 3:
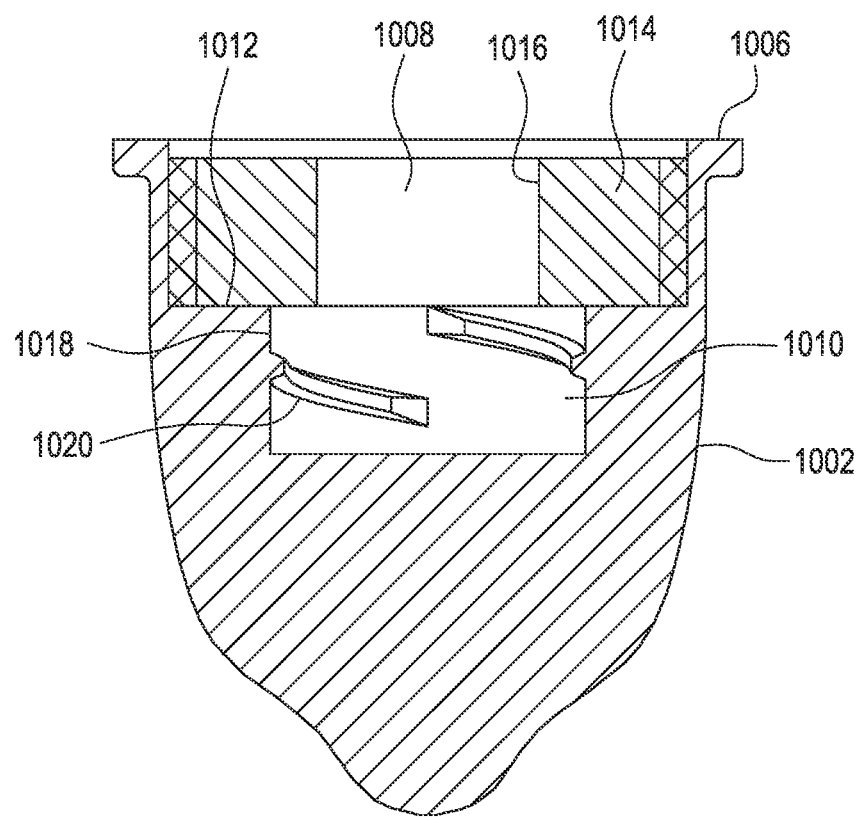
FIG. 3 shows a cross-sectional view along line A-A of the disinfecting cap of FIGS. 1-2.

FIGS. 1-3 show an illustrative disinfecting cap in accordance with embodiments of the invention. The cap 1002 is molded from PP. The cap includes an opening 1004 with a peripheral lip 1006. The opening 1004 provides access to a first cavity 1008 and a second cavity of smaller diameter 1010 extends from a base 1012 of the first cavity 1008. The cap may include ribs 1022 formed on an exterior surface to provide easier handling and twisting of the cap by a healthcare worker.

A foam ring 1014 is positioned within the first cavity 1008. The foam ring 1014 has a central bore 1016 extending through the ring. The central bore 1016 has a diameter that is smaller than the diameter of the second cavity 1010. The foam ring 1014 includes notches 1024 formed at intervals around the periphery of the ring, and the ring may be infused with a disinfecting solution. The second cavity 1010 includes threads 1020 formed on the inside diameter 1018 of the cavity.

Figure 4:
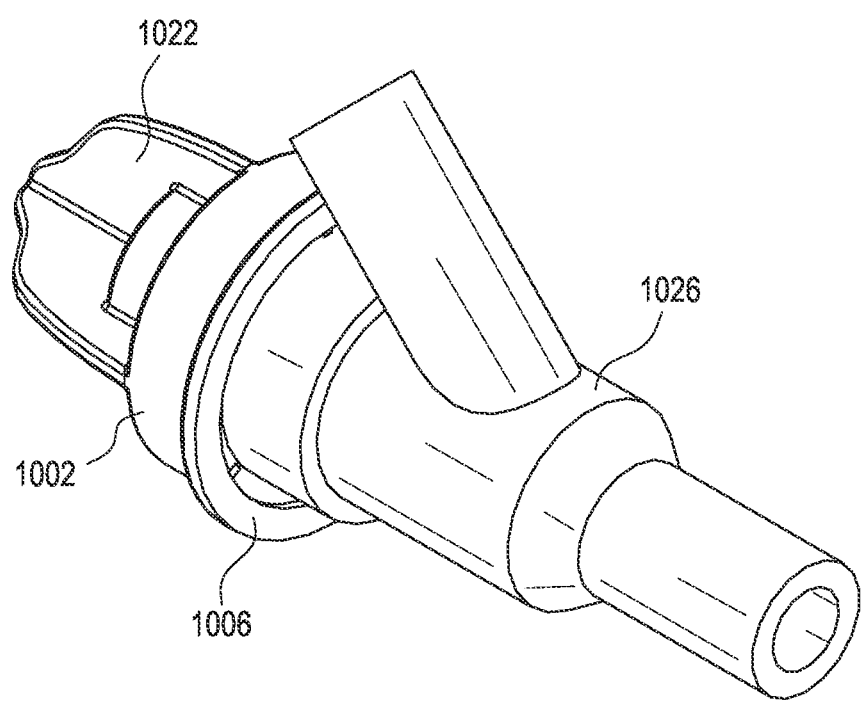
FIG. 4 shows a perspective view of the disinfecting cap of FIGS. 1-3 attached to a threaded female port of a Y-site.
Figure 5:
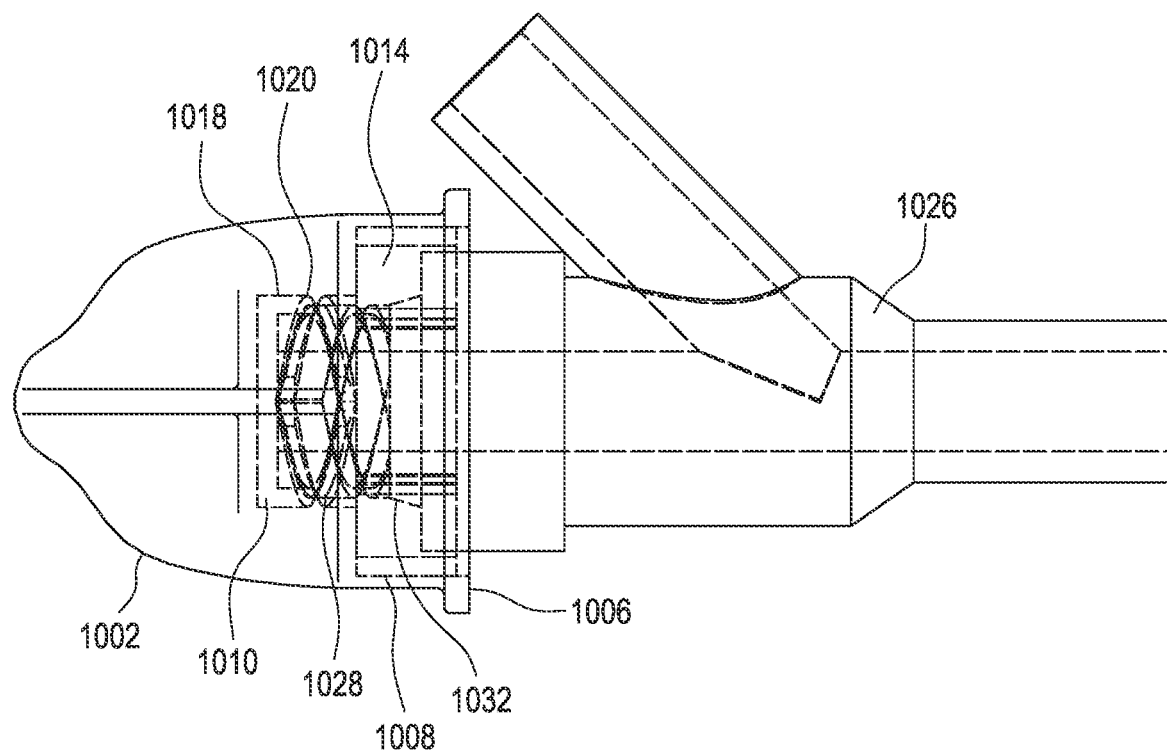
FIG. 5 shows a side view of the cap and Y-site of FIG. 4.

As shown in FIGS. 4-5, the cap 1002 may be attached to the threaded female port of a Y-site 1026. The female port is inserted through the bore 1016 of the foam ring 1014. The foam ring thereby wipes the outside surface of the port and applies a disinfecting solution. Threads 1028 formed on an outside diameter of the female port 1026 engage with the interior threads 1020 of the second cavity 1010, securing the cap to the port.

Figure 6:
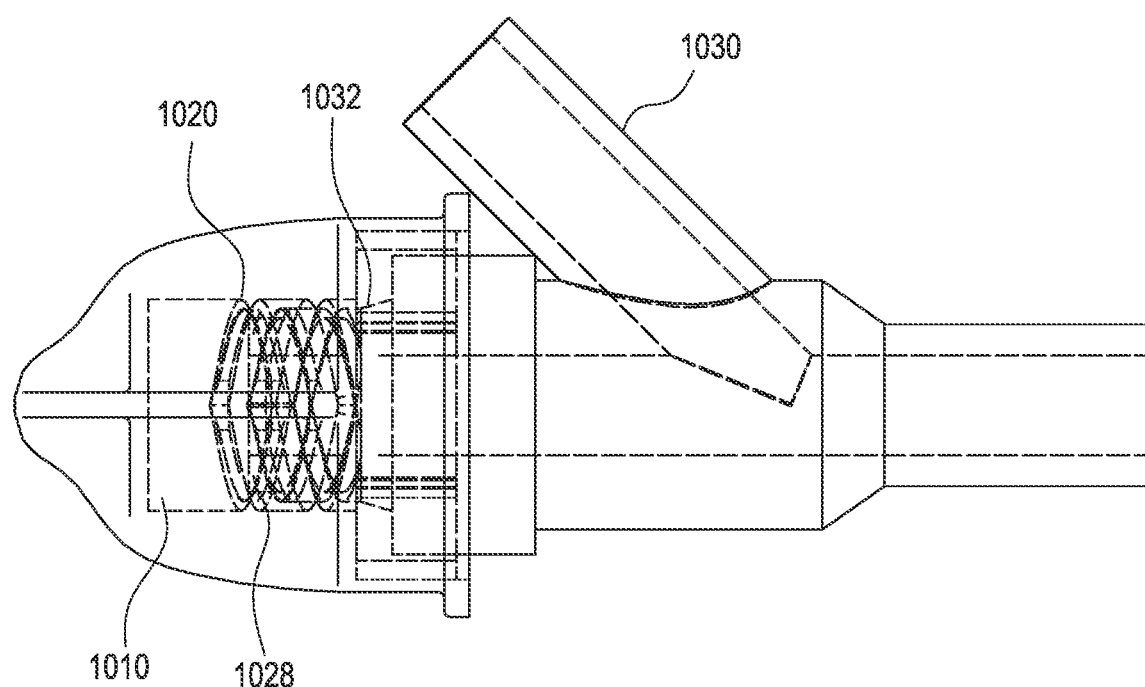
FIG. 6 shows a side view of a cap and Y-site in accordance with embodiments of the invention.

As shown in FIG. 5, the second cavity 1010 may have a depth such that the female port or its threads bottom out in the cavity before the cap 1002 contacts other portions of the Y-site. Alternatively, as shown in FIG. 6, the second cavity 1010 may be deeper such that the cap contacts the second port 1030 of the Y-site or such that a shoulder 1032 of the female port contacts the base 1012 of the first cavity surrounding the diameter of the second cavity.

Figure 7:
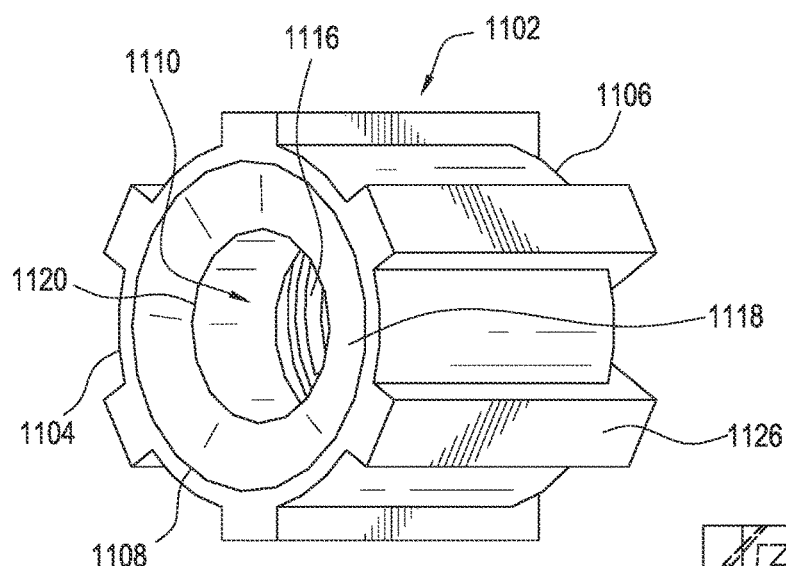
FIG. 7 shows a perspective view of a cap in accordance with embodiments of the invention.
Figure 8:
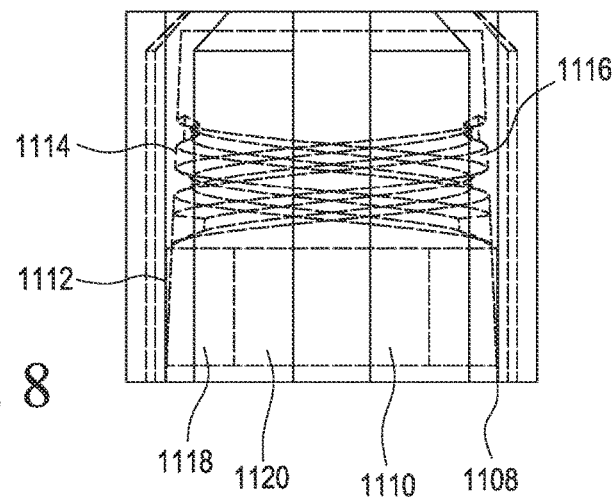
FIG. 8 shows a side view of the cap of FIG. 7.
Figure 9:
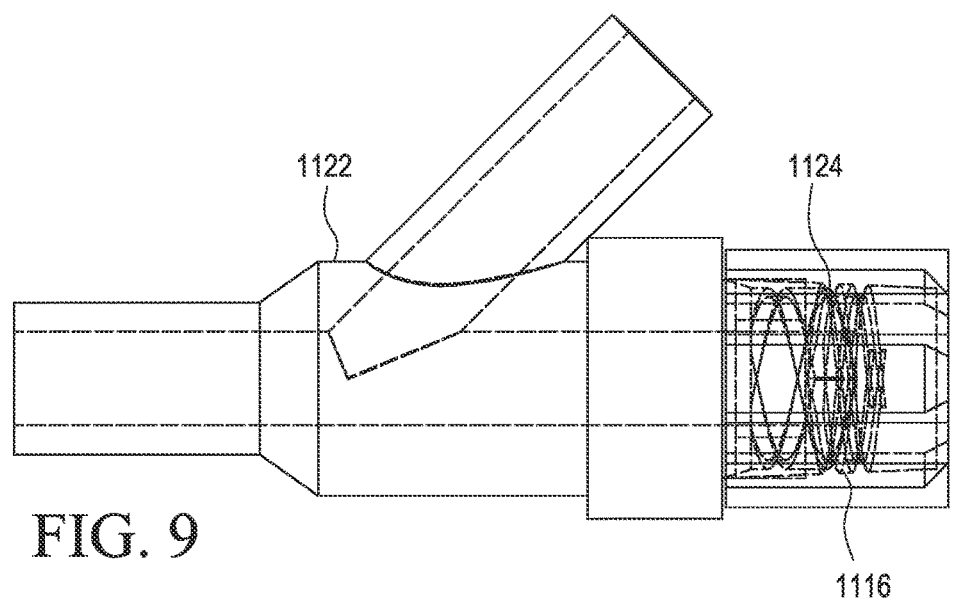
FIG. 9 shows a perspective view of the disinfecting cap of FIGS. 7-8 attached to a threaded female port of a Y-site.
Figure 10:
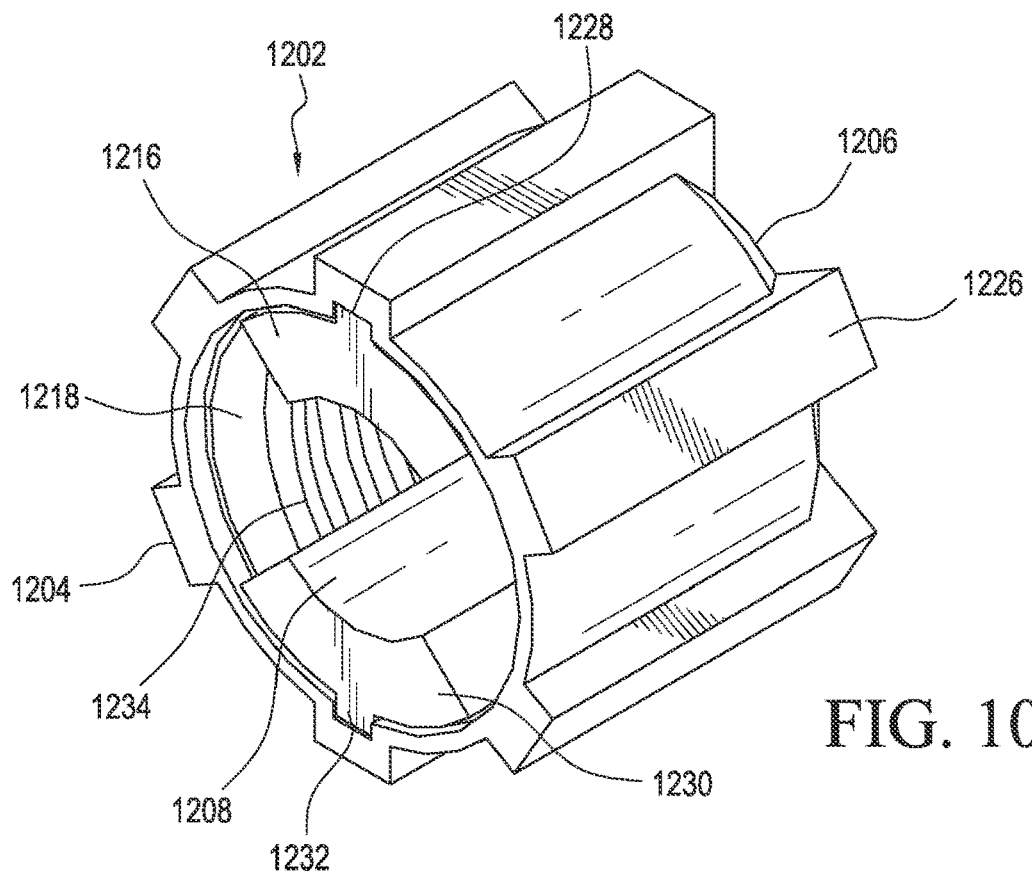
FIG. 10 shows a perspective view of a cap in accordance with embodiments of the invention.
Figure 11:
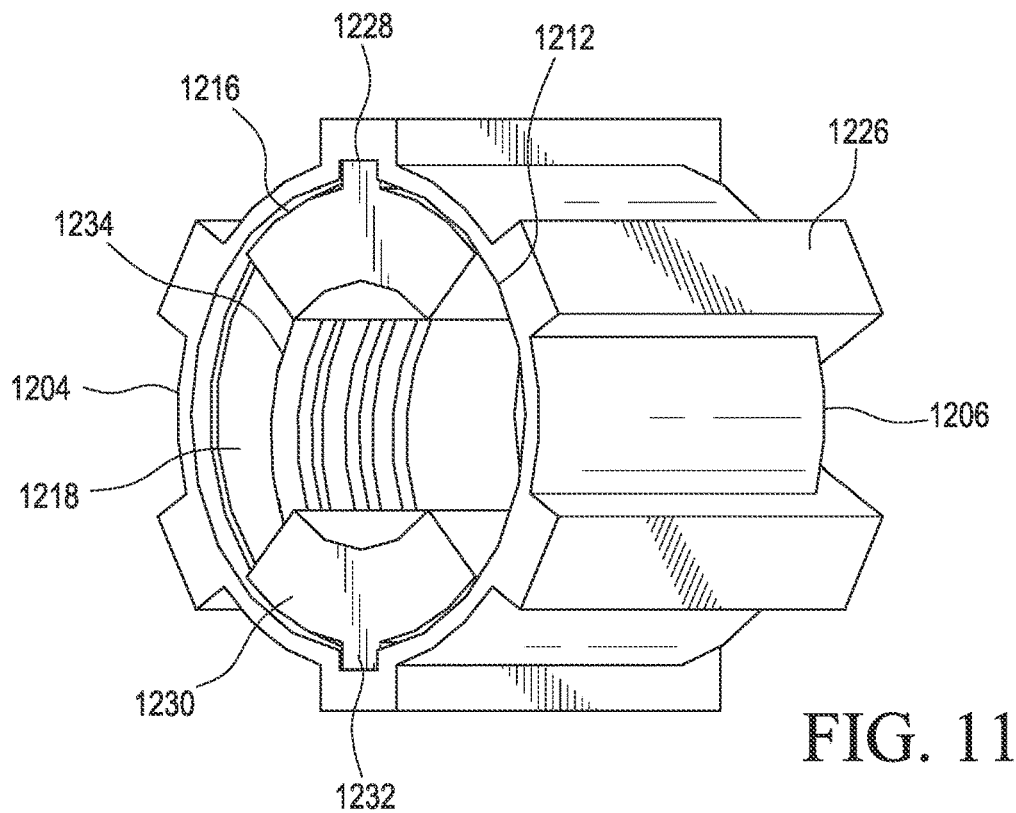
FIG. 11 shows another perspective view of the cap of FIG. 10.
Figure 12:
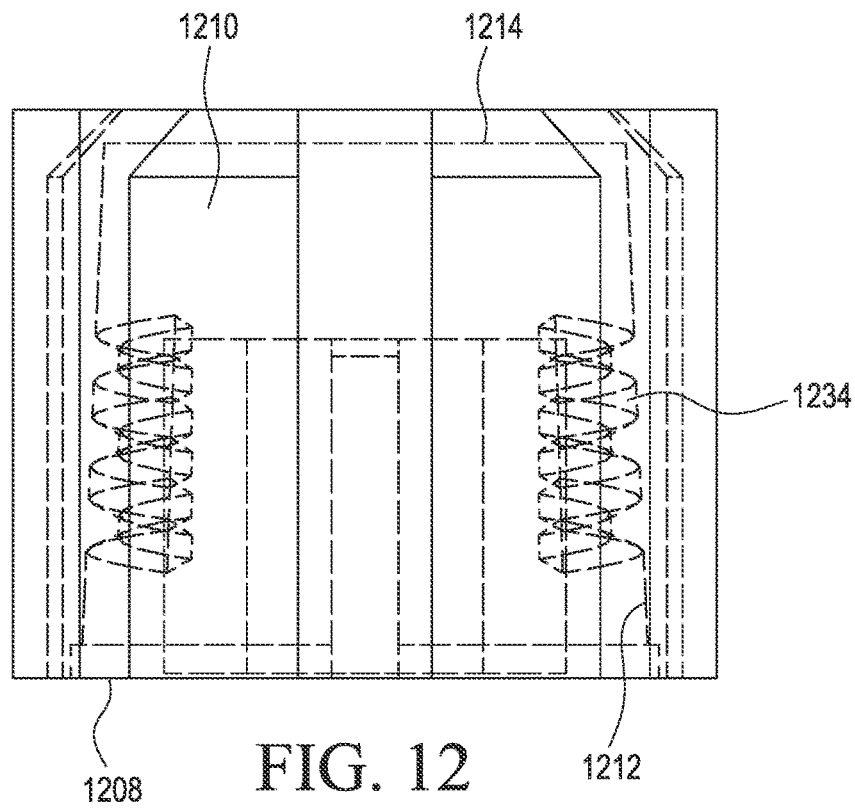
FIG. 12 shows a side view of the cap of FIGS. 10-11.
Figure 13:
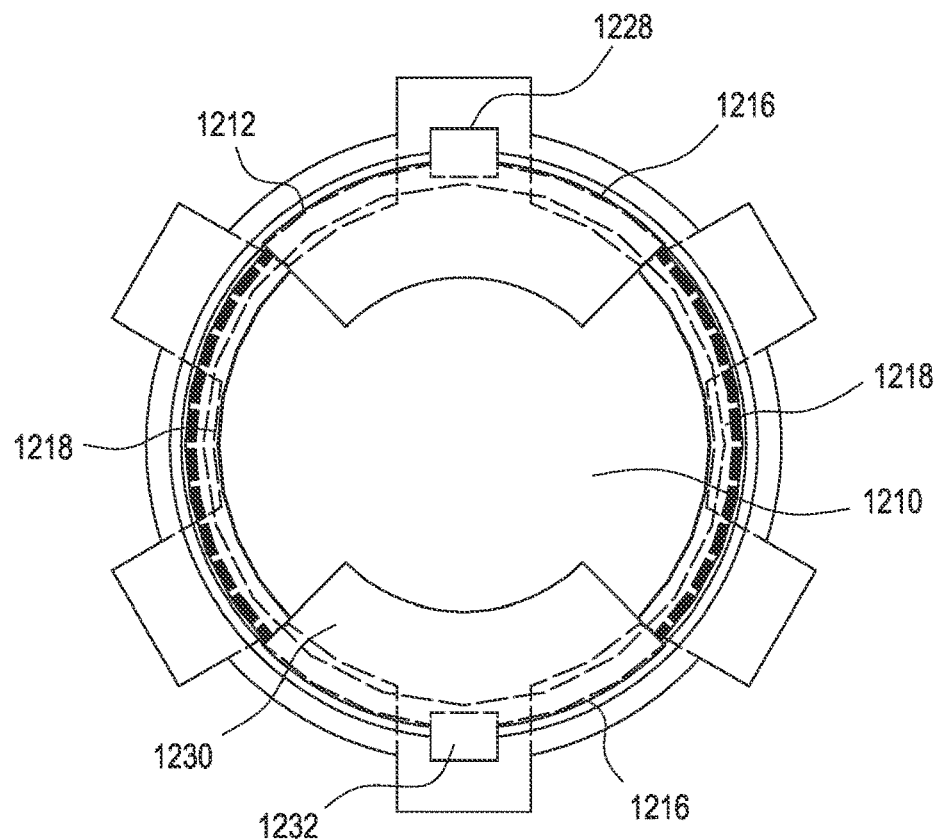
FIG. 13 shows a view of the proximal end of the cap of FIGS. 10-11.

FIGS. 7-9 show an illustrative disinfecting cap in accordance with embodiments of the invention. The cap 1102 may be molded from PP or another appropriate material. The cap includes an open proximal end 1104 and a closed distal end 1106. The cap 1102 may include ribs 1126 formed on an exterior surface to provide easier handling and twisting of the cap by a healthcare worker. The ribs may extend parallel to a central axis of the cap, as illustrated, or may have another configuration. Alternatively, other knurling, texturing, finger shaped or grip elements may be provided.

The proximal end has an opening 1108 that provides access to a cavity 1110. The cavity 1110 has a proximal section 1112 and a distal section 1114. The distal section 1114 may include threads 1116 formed on its interior diameter. A foam ring 1118 is inserted into the proximal cavity section 1112. The foam ring 1118 has a central bore 1120 extending through the ring. The ring 1118 extends a distance into the cavity 1110, but stops short of the threads 1116. The ring may be infused with a disinfecting solution.

As shown in FIG. 9, the cap 1102 may be attached to the threaded female port of a Y-site 1122. The female port of the Y-site is inserted through the bore 1120 of the foam ring 1118. The foam ring thereby wipes the outside surface of the port and applies a disinfecting solution. Threads 1124 formed on an outside diameter of the female port 1122 engage with the interior threads 1116 of the distal cavity 1114, securing the cap to the port.

FIGS. 10-13 show an illustrative disinfecting cap in accordance with embodiments of the invention. The cap 1202 may be molded from PP or another appropriate material. The cap includes an open proximal end 1204 and a closed distal end 1206. The cap 1202 may include ribs 1226 formed on an exterior surface to provide easier handling and twisting of the cap by a healthcare worker. The ribs may extend parallel to a central axis of the cap, as illustrated, or may have another configuration. Alternatively, other knurling, texturing, finger shaped or grip elements may be provided.

The proximal end has an opening 1208 that provides access to a cavity 1210. The cavity 1210 includes a generally cylindrical interior surface 1212. Though, the interior surface may be a conical section such that the diameter is larger adjacent to the opening 1208 than it is at the closed, distal end 1214 of the cavity. The interior surface 1212 is divided into sections, with each section encompassing at least a portion of the cylindrical surface. The sections include one or more foam sections 1216 and one or more thread sections 1218. Slots 1228 are formed in the foam sections 1218. The slots 1228 may extend generally parallel to a central axis of the cap.

Foam pieces 1230 are inserted into the cavity 1208 along foam sections 1216 of the interior surface. The foam pieces extend around the circumference of the cavity along the foam sections thereby forming a broken ring extending around at least a portion of the cavity interior circumference. A finger 1232 formed on an outer surface of each foam piece engages the slot 1228 and serves to hold the foam piece in place. The foam piece may be formed in a pre-curved manner or may take on a curved shape as a result of being installed against the curved circumference of the cavity. The foam piece may be infused with a disinfecting solution.

Threads 1234 are formed on the interior circumference of the thread sections 1218. The cap 1202 may be attached to the threaded female port of a Y-site (not shown). The female port of the Y-site is inserted through into the cavity 1208, and threads formed on an outside diameter of the female port engage with the interior threads 1234 of the distal cavity, securing the cap to the port. As the port is threaded into the cavity, the surface of the port passes over the foam pieces thereby wiping the outside surface of the port and applying a disinfecting solution.

Figure 14:
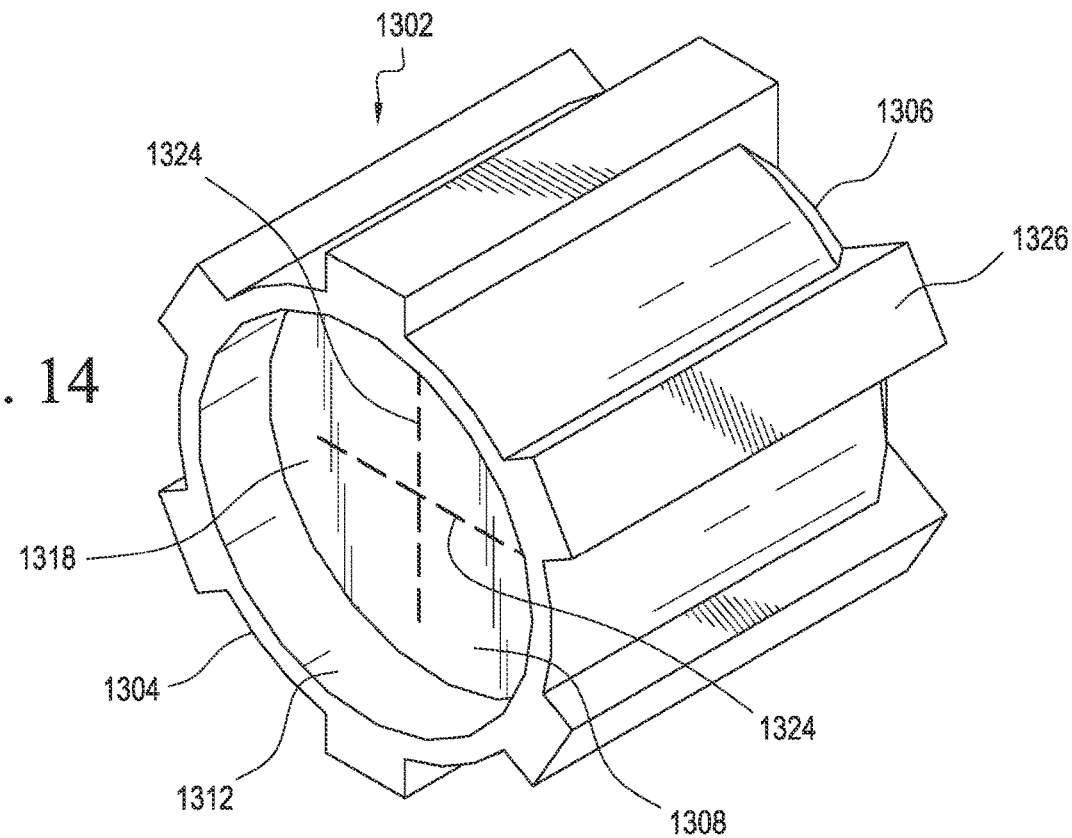
FIG. 14 shows a perspective view of a cap in accordance with embodiments of the invention.
Figure 15:
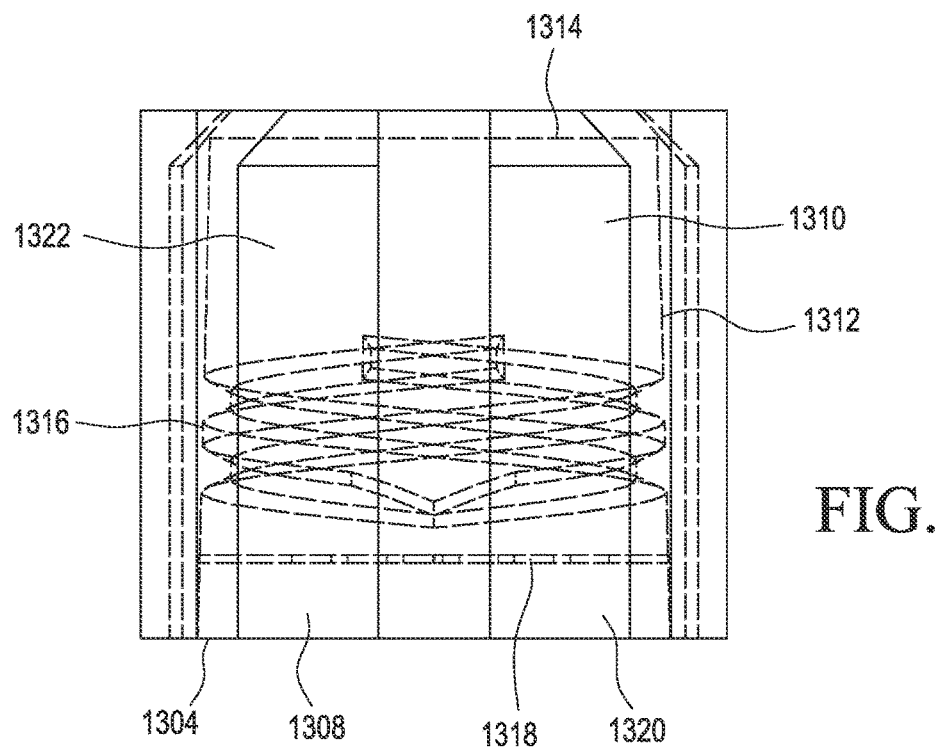
FIG. 15 shows a side view of the cap of FIG. 14.

FIGS. 14-15 show an illustrative disinfecting cap in accordance with embodiments of the invention. The cap 1302 may be molded from PP or another appropriate material. The cap includes an open proximal end 1304 and a closed distal end 1306. The cap 1302 may include ribs 1326 formed on an exterior surface to provide easier handling and twisting of the cap by a healthcare worker. The ribs may extend parallel to a central axis of the cap, as illustrated, or may have another configuration. Alternatively, other knurling, texturing, finger shaped or grip elements may be provided.

The proximal end has an opening 1308 that provides access to a cavity 1310. The cavity 1310 includes a generally cylindrical interior surface 1312. Though, the interior surface may be a conical section such that the diameter is larger adjacent to the opening 1308 than it is at the closed, distal end 1306 of the cavity. Threads 1316 are formed on the cavity interior surface 1312 and spaced some distance from the distal end 1306 of the cap.

A seal 1318 is positioned across the opening 1308 of the cavity 1310. The seal may be positioned adjacent to the proximal end 1304 of the cavity or may be spaced some distance into the cavity, leaving a space 1320 between the seal and the cap end. The space 1322 within the cavity that is enclosed by the seal 1318 may be at least partially filed with IPA. The seal may include perforations 1324, score lines or other features to aid in fracturing the seal.

The cap 1302 may be attached to the threaded female port of a Y-site (not shown). The female port of the Y-site is inserted through into the cavity 1308, and threads formed on an outside diameter of the female port engage with the interior threads 1316 of the cavity, securing the cap to the port. As force is applied to the cap to engage the port, the perforated seal breaks away under pressure from the port. The port surfaces are thereby exposed to liquid or vapor IPA.

Figure 16:
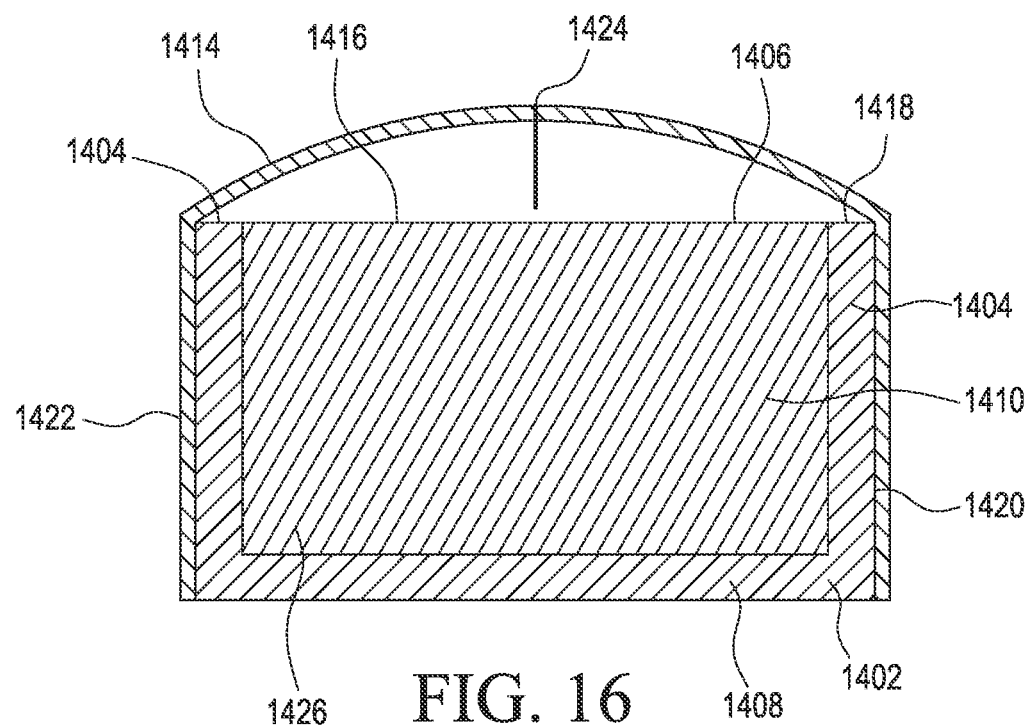
FIG. 16 shows a cross-sectional view of a cap in accordance with embodiments of the invention.
Figure 17:
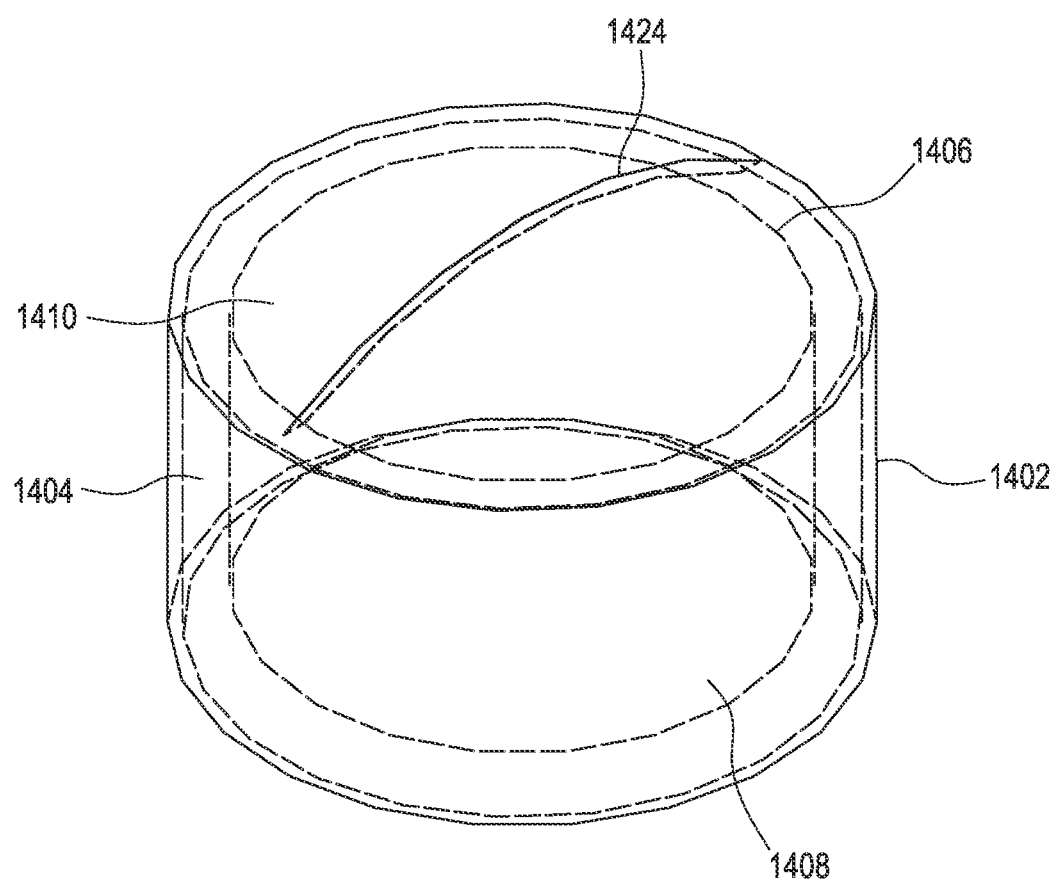
FIG. 17 shows a perspective view of the cap of FIG. 16.

FIGS. 16-17 show an illustrative disinfecting cap in accordance with embodiments of the invention. The cap 1402 may be formed of PP or another plastic. The cap includes side a generally cylindrical sidewall 1404. The cap includes an open proximal end 1406 and a closed distal end 1408 and encompasses a cavity 1410. The cap 1402 may include ribs (not shown) formed on an exterior surface to provide easier handling and twisting of the cap by a healthcare worker. The ribs may extend parallel to a central axis of the cap, as illustrated in other embodiments, or may have another configuration. Alternatively, other knurling, texturing, finger shaped or grip elements may be provided.

The cap further includes a diaphragm valve 1414 that covers the open end 1406 of the cavity 1410. The valve covers a proximal end 1418 of sidewall 1404 as well as the open end 1416 of the cavity 1410. A portion 1422 of the diaphragm valve 1414 may extend beyond the opening along an outside surface 1420 of sidewall 1404. The valve may be molded over the sides and open end of the cap. The diaphragm valve includes a slit 1424. A female port or other access site is pushed through the slit 1424 into the cavity 1410. The diaphragm valve secures the end of the port in the cavity once the port passes through the slit.

A portion of the cavity 1410 may be filled with IPA or another disinfecting substance in liquid or gel form. Alternatively, at least a portion of the cavity may be filled with a foam, such as an open cell PU foam 1426. The foam may be infused with a disinfecting substance.

Figure 18:
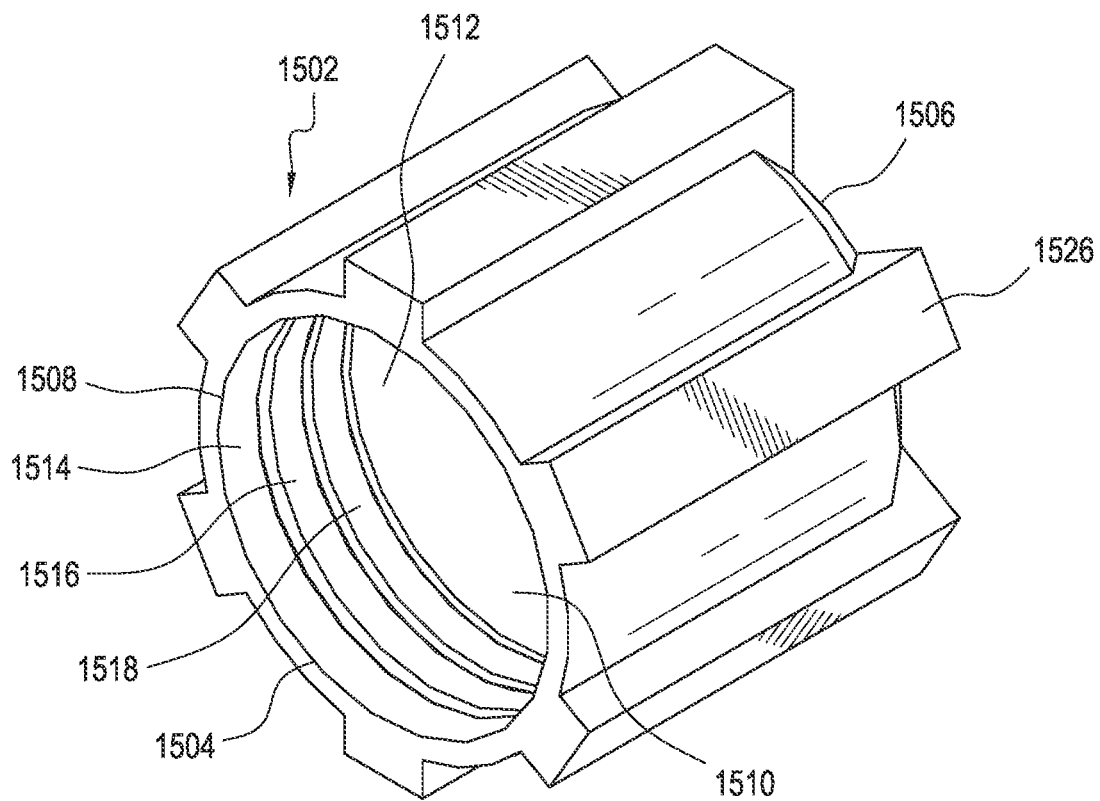
FIG. 18 shows a perspective view of a cap having a retention mechanism in accordance with embodiments of the invention.
Figure 19:
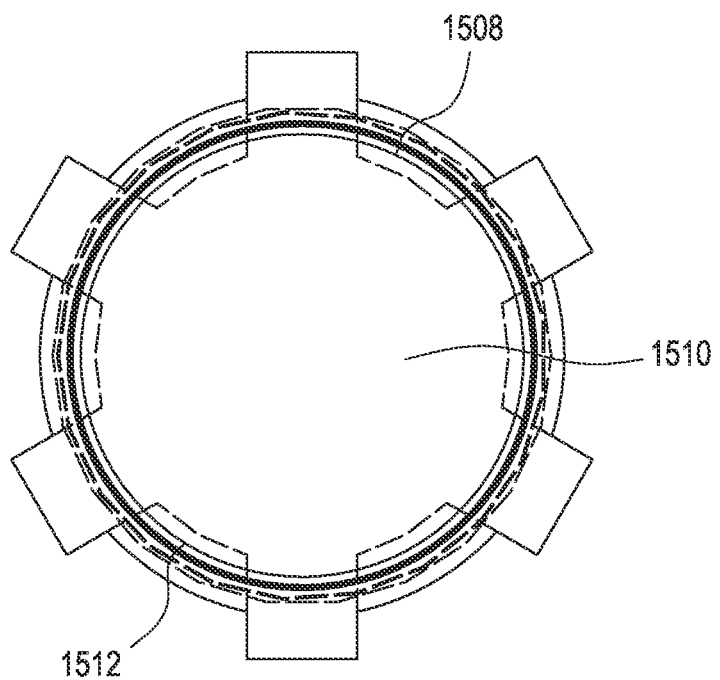
FIG. 19 shows a view of the proximal end of the cap of FIG. 18.

FIGS. 18-19 show an illustrative disinfecting cap having a retention mechanism in accordance with embodiments of the invention. Various embodiments of the invention as described in this application make use of threads formed on the outside of the site to be disinfected in order to secure the cap to the site. However, the present invention also contemplates the use of alternative securement mechanisms as illustrated, for example, in FIGS. 18-19. The cap 1502 an open proximal end 1504 and a closed distal end 1506. The cap 1502 may include ribs 1526 or other grip elements. The proximal end has an opening 1508 that provides access to a cavity 1510. The cavity 1510 includes a generally cylindrical interior surface 1512. Though, the interior surface may be a conical section such that the diameter is larger adjacent to the opening 1508 than it is at the closed, distal end 1504 of the cavity.

Adjacent the opening 1508, the interior surface includes a series of stepped counterbores 1514, 1516, 1518. Each successive counterbore has a small diameter than the previous. Accordingly, as illustrated in FIG. 18, the proximal counterbore 1514 adjacent to the opening has a first diameter, the next counterbore 1516 has a second small diameter and so on until the diameter of the interior surface 1512 is reached. The illustrative embodiment shows three different counterbores, but more or fewer could be used.

The counterbores 1514, 1516, 1518 are sized to engage a thread, shoulder or other portion of the site with a friction fit. Alternatively, the counterbores may provide clearance for a shoulder of the site so that interior surface 1512 may have an appropriate diameter to engage the threads of a port with a friction fit.

Figure 20:
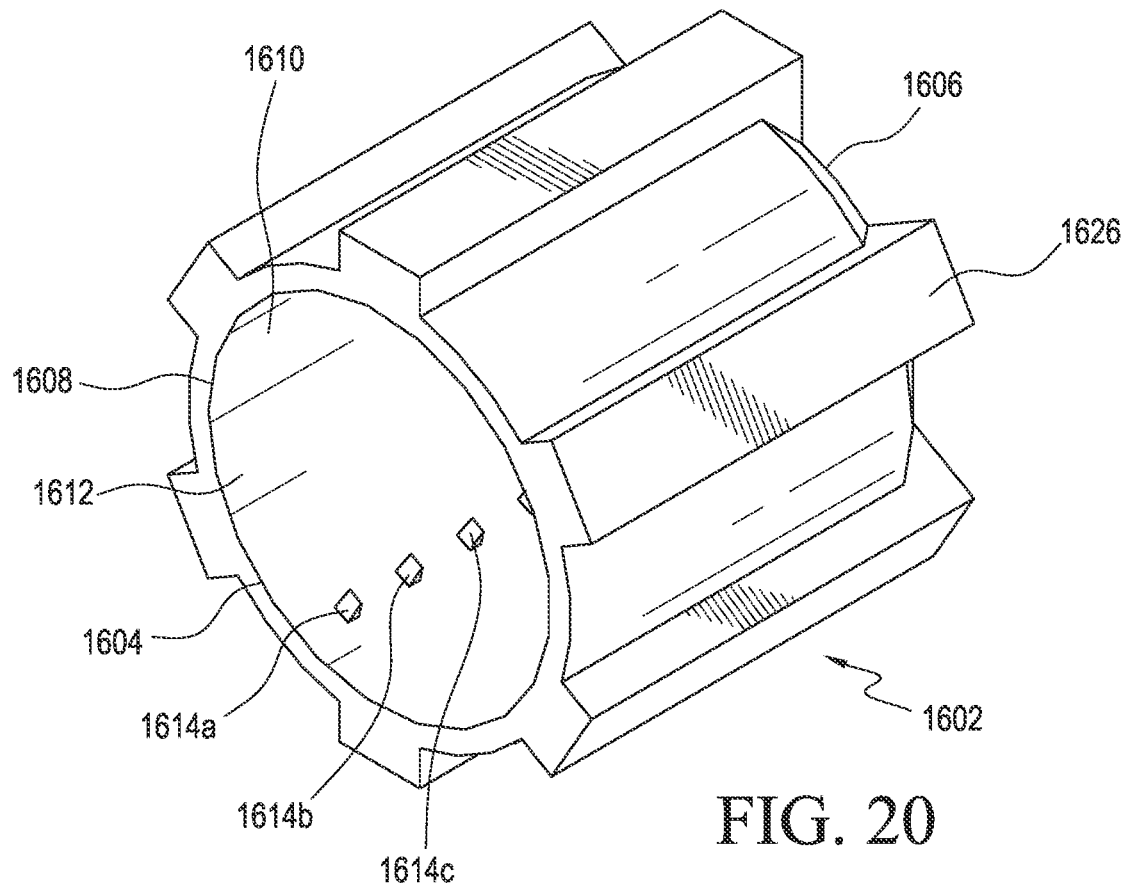
FIG. 20 shows a perspective view of a cap having a further retention mechanism in accordance with embodiments of the invention.
Figure 21:
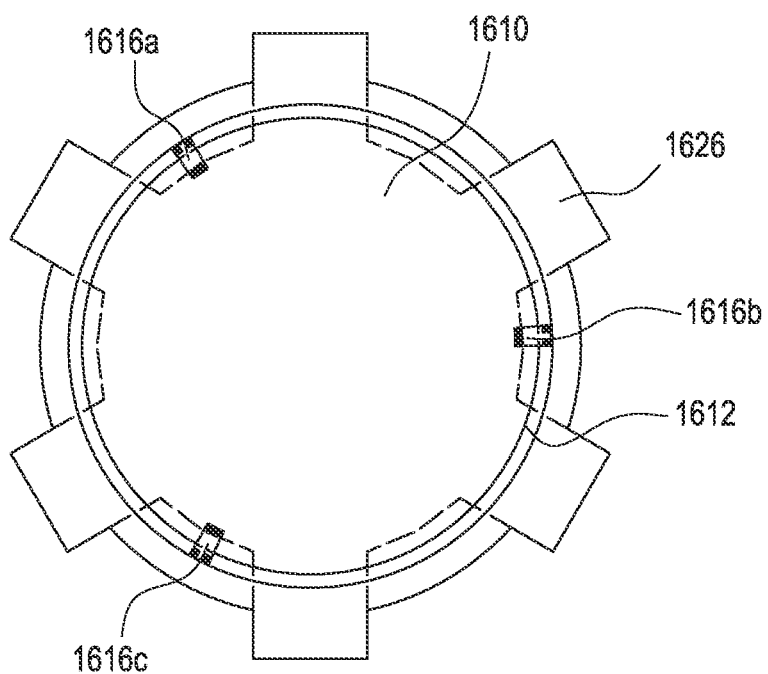
FIG. 21 shows a view of the proximal end of the cap of FIG. 20.
Figure 22:
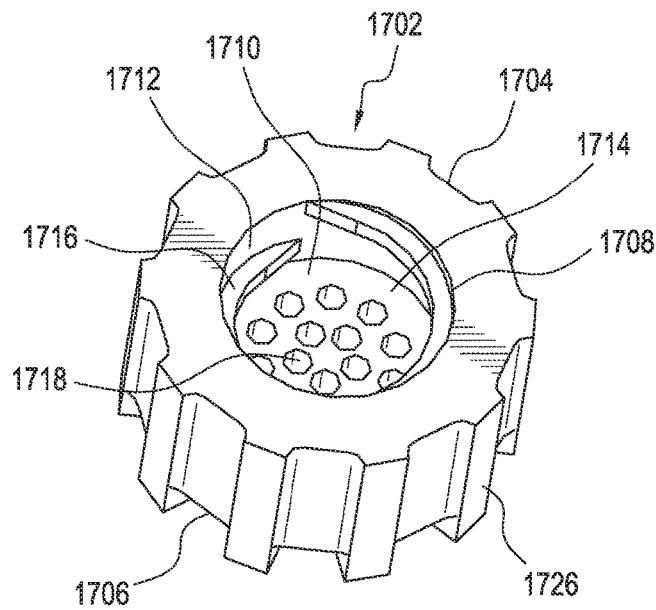
FIG. 22 shows a perspective view of disinfecting cap in accordance with embodiments of the invention.
Figure 23:
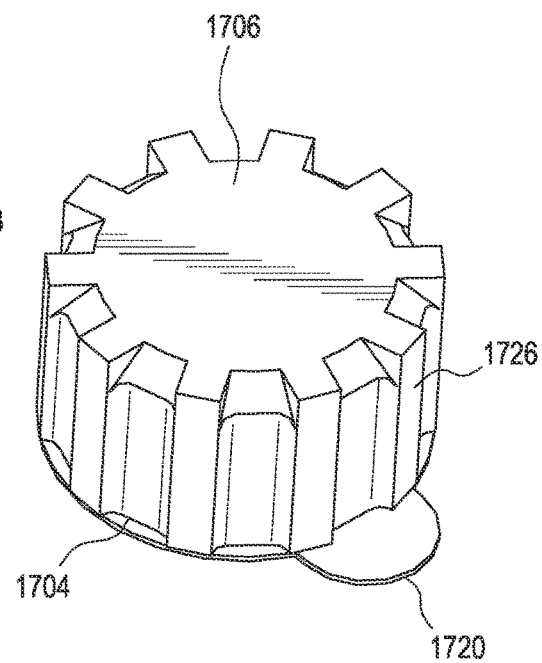
FIG. 23 shows a second perspective view of the disinfecting cap of FIG. 22.

FIGS. 20-21 show an illustrative disinfecting cap having an alternative retention mechanism in accordance with embodiments of the invention. The cap 1602 an open proximal end 1604 and a closed distal end 1606. The cap 1602 may include ribs 1626 or other grip elements. The proximal end has an opening 1608 that provides access to a cavity 1610. The cavity 1610 includes a generally cylindrical interior surface 1612. Though, the interior surface may be a conical section such that the diameter is larger adjacent to the opening 1608 than it is at the closed, distal end 1604 of the cavity.

Retention elements 1614 extend from the interior surface 1612. As illustrated in FIGS. 20-21, these elements are arranged in three columns 1616a, 1616b, 1616c spaced evenly around the interior surface. Though, more or fewer may be used. Within each column, a series of retention elements 1614a, 1614b, 1614c extends longitudinally into the cavity 1610 along the interior surface 1612. Arranged in this manner, the retention elements engage with the threads or other features of the port to be cleaned and retain the cap on the port. I In various embodiments, the retention elements may be formed in a resilient manner such that the cap can be pushed onto the port. As the threads of the port are pushed past each retention element, that element allows the thread to pass and then rebounds into a position in which the retention element engages the thread and retains the cap. Alternatively, the cap may be screwed onto the port such that the retention elements engage the threads.

The exemplary embodiment discussed herein contemplates arranging the retention elements 1614 in a certain pattern, particularly in equally columns of retaining elements. However, one of ordinary skill in the art would understand that the retaining elements could be arrange in any other possible patterns, including, among others, in a spiral pattern or a spaced matrix.

FIGS. 22-25 show an illustrative disinfecting cap in accordance with embodiments of the invention. The cap 1702 is molded from PU and may be reaction injection molded from PU foam into the final shape. The molded foam 1740 may include a skin 1742 that is resistant to IPA or other disinfecting solutions. The cap includes an open proximal end 1704 and a closed distal end 1706. The cap 1702 may include ribs 1726 formed on an exterior surface to provide easier handling and twisting of the cap by a healthcare worker. The ribs may extend parallel to a central axis of the cap, as illustrated, or may have another configuration. Alternatively, other knurling, texturing, finger shaped or grip elements may be provided.

The proximal end has an opening 1708 that provides access to a main cavity 1710. The cavity 1710 has a generally cylindrical sidewall 1712 and distal or bottom surface 1714. Threads 1716 may be formed on the sidewall in order to engage with the threads of a site to be cleaned and to retain the cap on the site. The cylindrical sidewall may have a constant diameter along a longitudinal axis of the cap or the diameter may increase along the longitudinal axis such that the diameter of the sidewall is greater at the distal end than the diameter of the sidewall at the proximal end at or near the bottom surface 1714 in one embodiment. In another embodiment the diameter may decrease along the longitudinal axis such that the diameter of the sidewall is smaller at the distal end than the diameter of the sidewall at the proximal end at or near the bottom surface 1714.

One or more depressions, cavities or holes 1718 are formed extending into the cap from the distal surface 1714 of the cavity 1710. These holes 1718 are at least partially filled with and serve as reservoirs to retain a disinfecting solution such as liquid or gel ISA. When inserted into the cap, the end surface of the site may come in contact with the distal surface 1714 of the cavity 1710 such that the site is wetted by the disinfecting solution, or the surface of the site may remain spaced from the distal surface such that disinfecting is provided by disinfecting solution vapor contained within the cap.

The cap 1702 may include a peelable lid 1720 that is sealed to the skin 1742 of the cap in order to retain the disinfecting solution within the cap cavity 1710, thereby preventing the disinfecting solution from leaking or evaporating out from the cap 1702.

Figure 24:
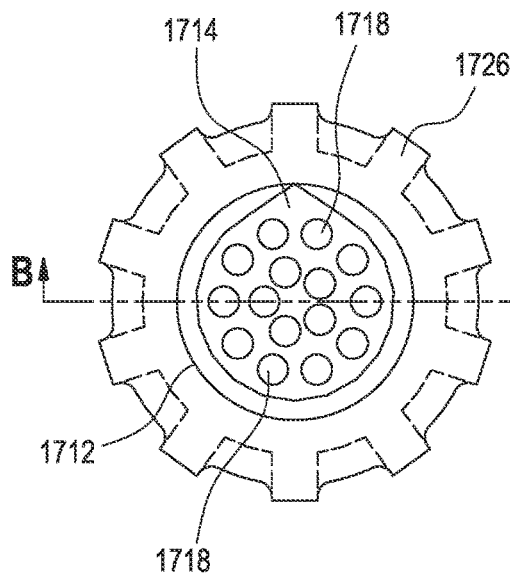
FIG. 24 shows a view of the proximal end of the cap of FIG. 22.
Figure 25:
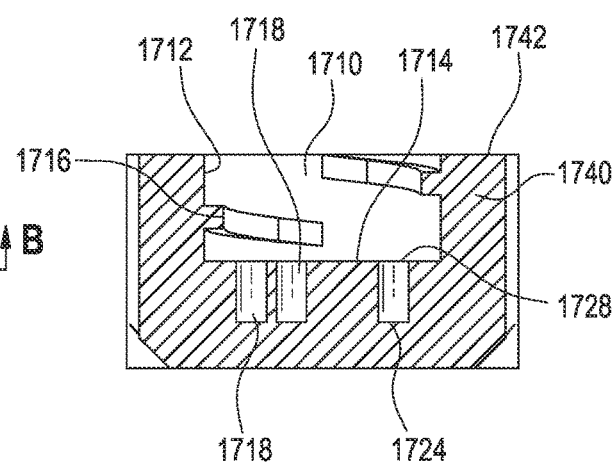
FIG. 25 shows a cross-sectional view along line B-B of the disinfecting cap of FIG. 22.
Figure 29:
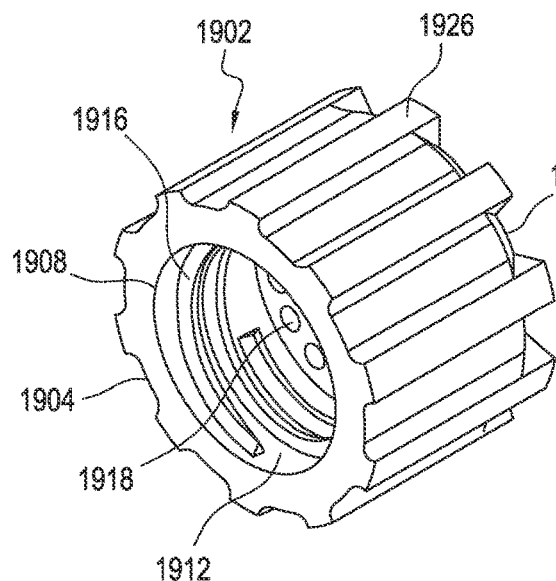
FIG. 29 shows a perspective view of disinfecting cap in accordance with embodiments of the invention.
Figure 30:
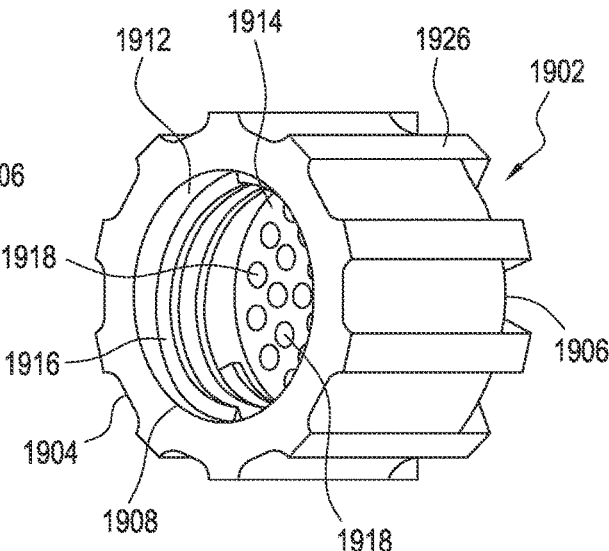
FIG. 30 shows a second perspective view of the disinfecting cap of FIG. 29.

The holes 1718 may be generally cylindrical in shape and may be arranged in any appropriate pattern. Alternatively, the holes may be formed in other shapes. For example, FIGS. 27-28 show an illustrative embodiment of a cap 1802 that has similarities to the embodiment of FIGS. 22-26 in which the holes 1818 are spaced farther from sidewall 1812 and are generally rectangular in profile. The holes may be formed with a constant cross-section as illustrated in FIGS. 24-25 and 28, or the holes may have a different cross-section. For example, the holes may have a conical or pyramid shape such that the opening 1728 adjacent to the distal surface 1714, 1814 of the cavity 1710, 1810 has a greater cross-sectional area than the bottom 1724 of the hole 1718. Alternatively, the hole may have an undercut such that the opening adjacent to the distal surface 1714, 1814 of the cavity 1710, 1810 has a smaller cross-sectional area than the bottom 1724 of the hole 1718. The shape or geometry of the hole may be such that the surface tension (cohesion and adhesion) of the disinfecting solution is held inside the hole below the distal surface 1714, 1814 without the need for a cover or other retaining mechanism.

In one embodiment, the disinfecting solution in the cap fills the individual cavities 1718 as well as at least a portion of the main cavity 1710. Applicants have surprisingly found that a cap having this configuration, namely multiple cavities in the bottom surface in conjunction with a main cavity, causes the cap to significantly retain a greater volume of solution, particularly when inverted than is achieved with a cap having a single main cavity portion. This allows the cap to be inverted when being installed on a port while still retaining a sufficient volume of solution. Such a cap retains sufficient solution even when the cap is shaken. This result is found both in caps that employ internal threads and in caps that do not have threads but rather use a constant diameter cylindrical sidewall cavity that engages the port by a friction fit.

In tests performed using a cap having a honeycomb depth of 2.5 mm, initial testing shows honeycomb structure retains 50% more IPA while inverted than a cap without honeycomb or some other fluid retention mechanism. In additions, the honeycomb was able to retain 70% of the inverted IPA following vigorous shaking.

FIGS. 29-32 show an illustrative disinfecting cap in accordance with embodiments of the invention. The cap includes an open proximal end 1904 and a closed distal end 1906. The cap 1902 may include ribs 1926 formed on an exterior surface to provide easier handling and twisting of the cap by a healthcare worker. The ribs may extend parallel to a central axis of the cap, as illustrated, or may have another configuration. Alternatively, other knurling, texturing, finger shaped or grip elements may be provided.

The proximal end has an opening 1908 that provides access to a cavity 1910. The cavity 1910 has a generally cylindrical sidewall 1912 and distal or bottom surface 1914. Threads 1916 may be formed on the sidewall in order to engage with the threads of a site to be cleaned and to retain the cap on the site. The threads may extend completely around the internal circumference of the inner cavity, they may extend partially around, or they may extend greater than once around the entire internal circumference.

One or more depressions, cavities or holes 1918 are formed extending into the cap from the distal surface 1914 of the cavity 1910. These holes 1918 are at least partially filled with and serve as reservoirs to retain a disinfecting solution such as liquid or gel ISA. The holes 1918 may be generally cylindrical in shape and may be arranged in any appropriate pattern. Alternatively, the holes may be formed in other shapes.

Figure 31:
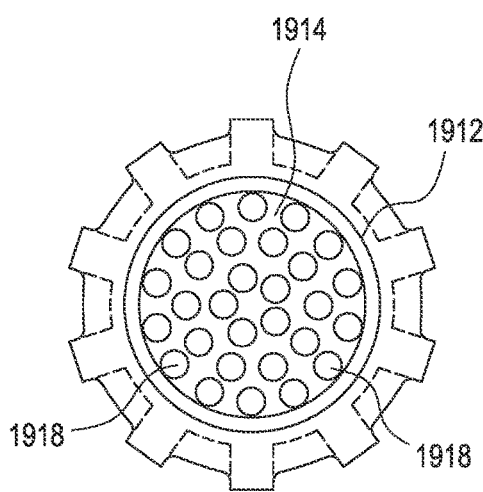
FIG. 31 shows a view of the proximal end of the cap of FIG. 29.
Figure 32:
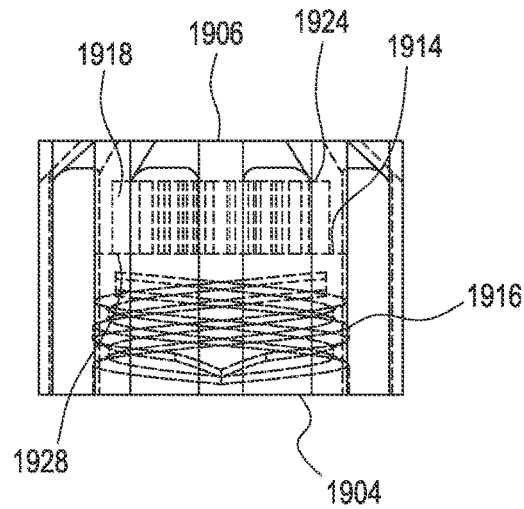
FIG. 32 shows a side view of the disinfecting cap of FIG. 29.

The holes may be formed with a constant cross-section as illustrated in FIGS. 31-32, or the holes may have a different cross-section. For example, the holes may have a conical or pyramid shape such that the opening 1928 adjacent to the distal surface 1914 of the cavity 1910 has a greater cross-sectional area than the bottom 1924 of the hole 1918. Alternatively, the hole may have an undercut such that the opening 1928 adjacent to the distal surface 1914 of the cavity 1910 has a smaller cross-sectional area than the bottom 1924 of the hole 1918. The shape or geometry of the hole may be such that the surface tension (cohesion and adhesion) of the disinfecting solution is held inside the hole below the distal surface 1914 without the need for a cover or other retaining mechanism when the cap is in use.

However, as illustrated in FIG. 36, the cap may include a peelable lid 1950 or other packaging. A portion 1952 of the lid 1950 extends into the cavity 1910 of the cap 1902. An inside surface of the extending portion 1952 of the lid may seal against the bottom surface of the cavity 1910 to retain the disinfecting solution in the holes until the cap is used.

Figure 33:
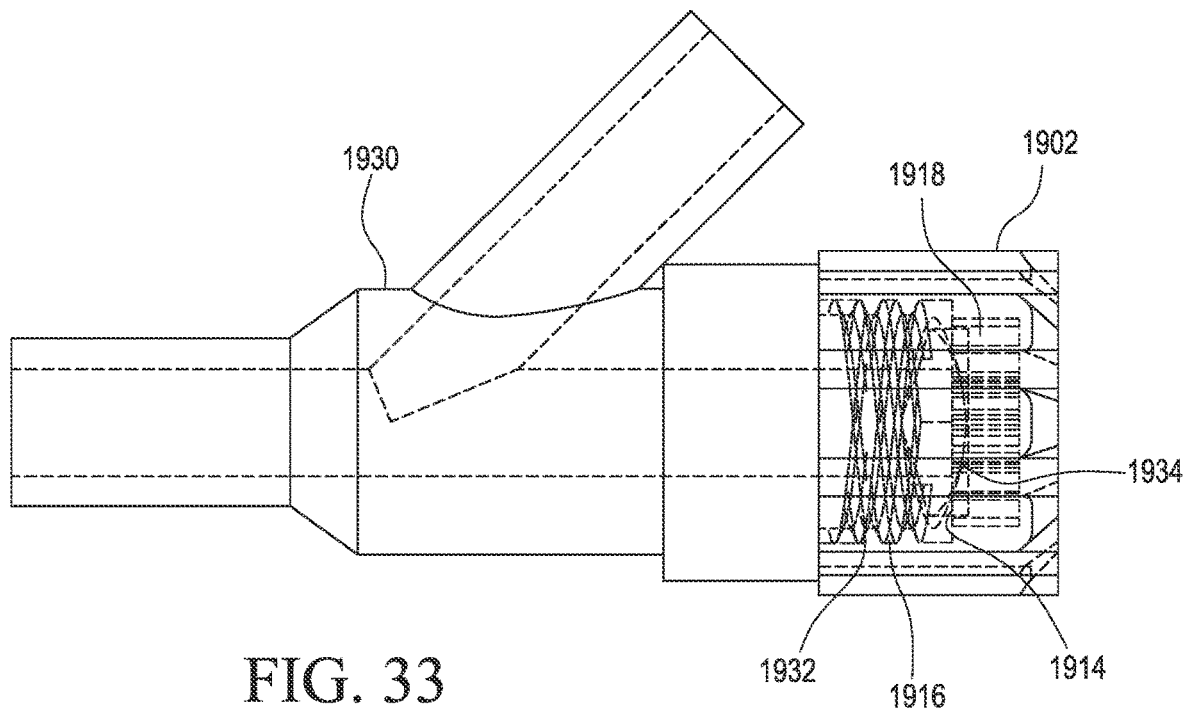
FIG. 33 shows a side view of the disinfecting cap of FIG. 29 attached to a threaded female port of a Y-site.

As shown in FIG. 33, the cap 1902 may be attached to the threaded female port of a Y-site 1930. The female port of the Y-site is inserted into the cavity 1910 of the cap. Threads 1932 formed on an outside diameter of the female port 1930 engage with the interior threads 1916, securing the cap to the port.

When inserted into the cap, the end surface 1934 of the site may come in contact with the distal surface 1914 of the cavity 1910 such that the site is wetted by the disinfecting solution. As the face 1934 of the connector engages the bottom surface 1914 of the cavity 1910, the bottom surface 1914 and hole openings 1928 are distorted and disinfecting solution releases from the holes 1918 as the holes deform and lose their full volume. The material of the entire cap or of only a section surrounding the holes 1918 at the bottom of the cavity 1910 may be soft or hard plastic, such as polypropylene (PP) or santoprene or other thermoplastic elastomers (TPE). Alternatively, the surface of the site may remain spaced from the distal surface such that disinfecting is provided by disinfecting solution vapor contained within the cap.

Figures 34, 35:
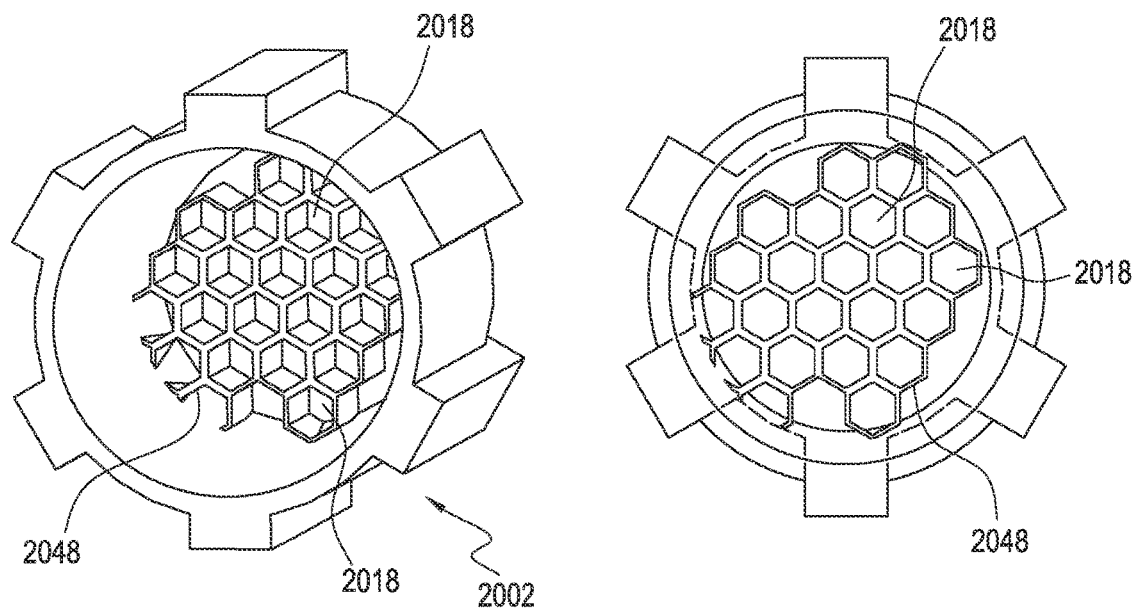
FIG. 34 shows a perspective view of disinfecting cap in accordance with embodiments of the invention.
FIG. 35 shows a view of the proximal end of the cap of FIG. 34.

FIGS. 34-35 show an illustrative embodiment of a cap 2002 that has similarities to the embodiment of FIGS. 29-33 in which the holes 2018 are formed as a honeycomb 2048 rather than as individual cavities.

FIGS. 40-42 show a further illustrative embodiment of a cap 2802 that has similarities to the embodiment of FIGS. 34-35. In this exemplary embodiment, the cap includes an open proximal end 2804 and a closed distal end 2806. The cap 2802 may include ribs 2826 formed on an exterior surface to provide easier handling and twisting of the cap by a healthcare worker. The ribs may extend parallel to a central axis of the cap, as illustrated, or may have another configuration. Alternatively, other knurling, texturing, finger shaped or grip elements may be provided.

The proximal end has an opening 2808 that provides access to a cavity 2810. The cavity 2810 has a generally cylindrical sidewall 2812 and distal or bottom surface 2814. Threads 2816 may be formed on the sidewall in order to engage with the threads of a site to be cleaned and to retain the cap on the site. The threads may extend completely around the internal circumference of the inner cavity, they may extend partially around, or they may extend greater than once around the entire internal circumference. In the illustrative embodiment, the threads are shown extending up to the surface of the proximal end 2804 of the cap.

Hexagonal cavities or holes 2818 similar to a honeycomb are formed extending into the cap from the distal surface 2814 of the cavity 2810. These holes 2818 are at least partially filled with and serve as reservoirs to retain a disinfecting solution such as liquid or gel ISA.

The holes may be formed with a constant cross-section as illustrated in FIGS. 40-42, or the holes may have a varying cross-section. For example, the holes may have a conical or hexagonal-pyramid shape such that the opening 2828 adjacent to the distal surface 2814 of the cavity 2810 has a greater cross-sectional area than the bottom 2824 of the hole 2818. Alternatively, the hole may have an undercut such that the opening 2828 adjacent to the distal surface 2814 of the cavity 2810 has a smaller cross-sectional area than the bottom 2824 of the hole 2818. The shape or geometry of the hole may be such that the surface tension (cohesion and adhesion) of the disinfecting solution is held inside the hole below the distal surface 2814 without the need for a cover or other retaining mechanism when the cap is in use.

FIGS. 37-39 show an illustrative disinfecting cap in accordance with embodiments of the invention. The cap 2102 includes a lanyard 2104 that can be used to hang or otherwise attaché the cap to the port or access site to be cleaned. The lanyard has a loop 2106 through which the port can be inserted. The cap may include two cap portions 2108, 2110 such that the cap can be used twice. Each cap portion has a generally cylindrical side wall 2112, and open end 2114 and a closed end 2116. The caps are position back-to-back such that the closed end 2116 is shared. The cap 2102 is removed from any packaging, and the first cap portion 2108 is applied to the port to be cleaned. Even when removed from the initial packaging, the second cap portion 2110 includes a sealed lid 2118. When the healthcare worker uses the cap for a second time, the lid 2118 is removed, and the second cap portion 2110 is applied to the port to be cleaned.

Figures 43, 44A, 44B:
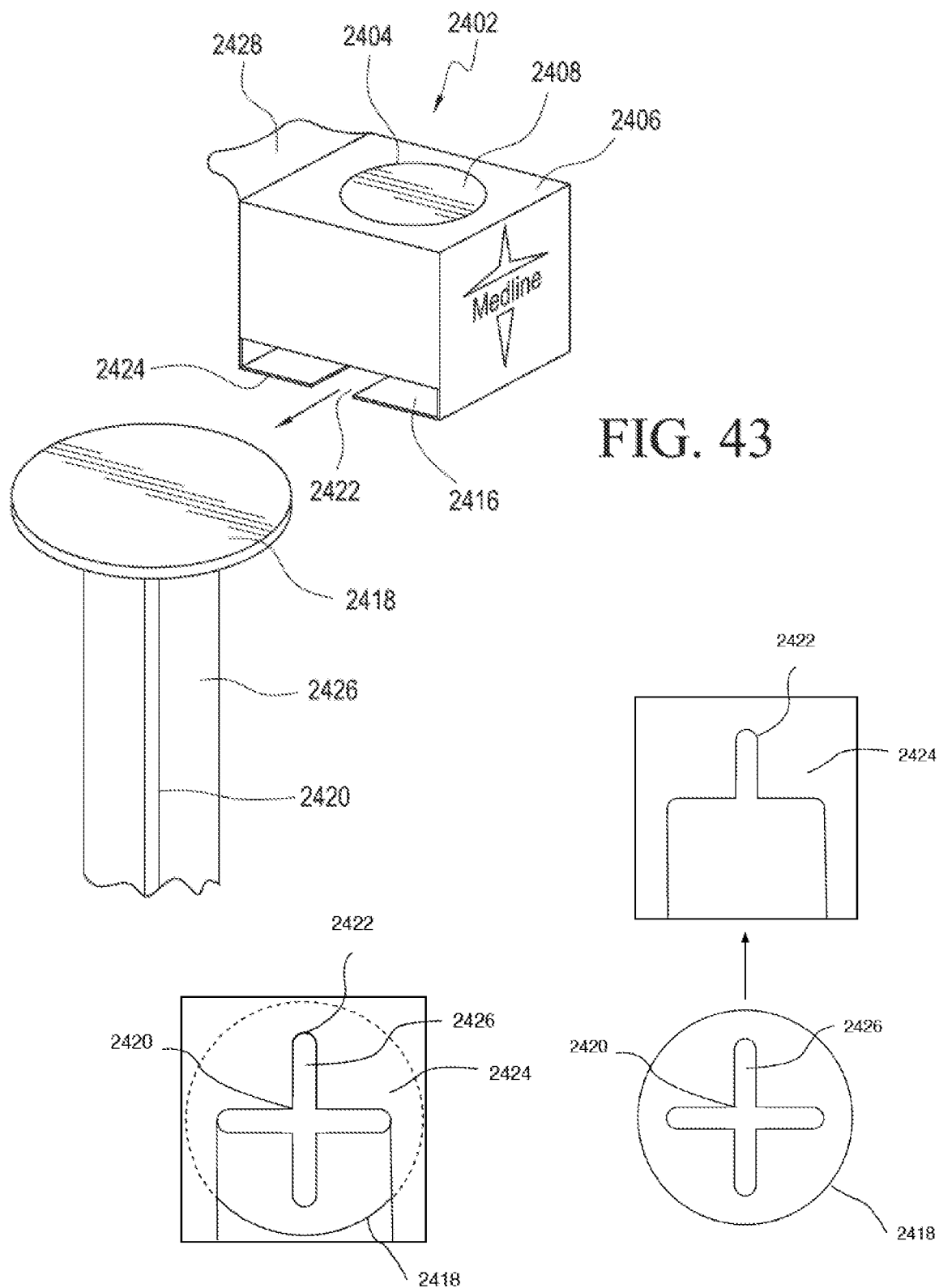
FIG. 43 shows a perspective view of disinfecting cap in accordance with embodiments of the invention.
FIGS. 44A and 44B show a bottom view of the disinfecting cap of FIG. 43.

FIGS. 43-45 show an illustrative disinfecting cap in accordance with embodiments of the invention. The cap 2402 may be molded from PP or another appropriate plastic or other material. The cap includes an opening 2404 with a peripheral surface 2406 surrounding the opening. The opening 2404 provides access to a cavity 2408.

The cap 2402 may have a generally square cross-section or may include ribs formed on an exterior surface to provide easier handling and twisting of the cap by a healthcare worker. The ribs may extend parallel to a central axis of the cap or may have another configuration. Alternatively, other knurling, texturing, finger shaped or grip elements may be provided.

The cavity 2408 has a generally cylindrical sidewall 2412 and distal or bottom surface 2414. Retention elements 2410 extend from the interior surface 2412. In various embodiments, the retention elements may be formed in a resilient manner such that the cap can be pushed onto the port. As the threads of the port are pushed past each retention element, that element allows the thread to pass and then rebounds into a position in which the retention element engages the thread and retains the cap. Alternatively, the cap may be screwed onto the port such that the retention elements engage the threads.

One of ordinary skill in the art would understand that the retaining elements 2410 could be arrange in any number of possible patterns, including, among others, in columns, rows a spiral pattern or a spaced matrix. Alternatively, threads may be formed on the sidewall in order to engage with the threads of a site to be cleaned and to retain the cap on the site.

The cylindrical sidewall may have a constant diameter along a longitudinal axis of the cap or the diameter may increase along the longitudinal axis such that the diameter of the sidewall is greater at the proximal end than the diameter of the sidewall at the distal end at or near the bottom surface 2414 in one embodiment. In another embodiment the diameter may decrease along the longitudinal axis such that the diameter of the sidewall is smaller at the proximal end than the diameter of the sidewall at the distal end at or near the bottom surface 2414.

The cap 2402 may include an aperture 2416 adjacent the bottom or distal end of the cap. The aperture may be sized to accept the thumb pad 2418 attached to the plunger actuating shaft 2420 of a syringe (not shown). The bottom surface 2424 enclosing the aperture 2416 may include a slot 2422 that is of an appropriate size to accommodate a rib 2426 of the syringe plunger shaft 2420.

An absorbent material 2430 may be positioned inside the cavity 2408. The absorbent material may be infused with a disinfecting solution. Alternatively, the disinfecting solution may be present in the cavity without the use of an absorbent material. The cap 2402 may include a peelable lid 2428 that is sealed to the top surface 2406 of the cap in order to retain the disinfecting solution within the cap cavity 2408, thereby preventing the disinfecting solution from leaking or evaporating out from the cap 2402.

FIG. 46 shows an illustrative disinfecting cap in accordance with embodiments of the invention. In this embodiment, the cap 2502 includes resilient fingers 2516 extending from a bottom surface 2524 of the cap. One or more slots 2522 may extend vertically between the resilient fingers 2516 so that the fingers can flex outward to accommodate the thumb pad 2518 attached to the plunger actuating shaft 2520 of a syringe 2532. The fingers 2516 may include a notch or groove 2534 in which the thumb pad seats when the cap is installed. In the illustrated embodiment, the opening 2504 of the cap is positioned on the distal end 2536 of the cap away from the syringe 2532.

FIG. 47 shows an illustrative disinfecting cap in accordance with embodiments of the invention. In this embodiment, the cap 2602 may be formed of a soft or flexible material. The cap includes a lip 2616 that is stretched to extend around at least a portion of the diameter of the thumb pad 2618 attached to the plunger actuating shaft 2620 of a syringe (not shown). The cap 2602 includes a cavity 2608 having an opening 2604 and a closed end 2614. In the illustrated embodiment, a top surface 2606 of the cap surrounding the opening 2604 is positioned adjacent the surface of the thumb pad 2618. In this manner, the thumb pad may act to seal the cavity 2608 in order to retain the disinfecting solution within the cap cavity.

Figure 48:
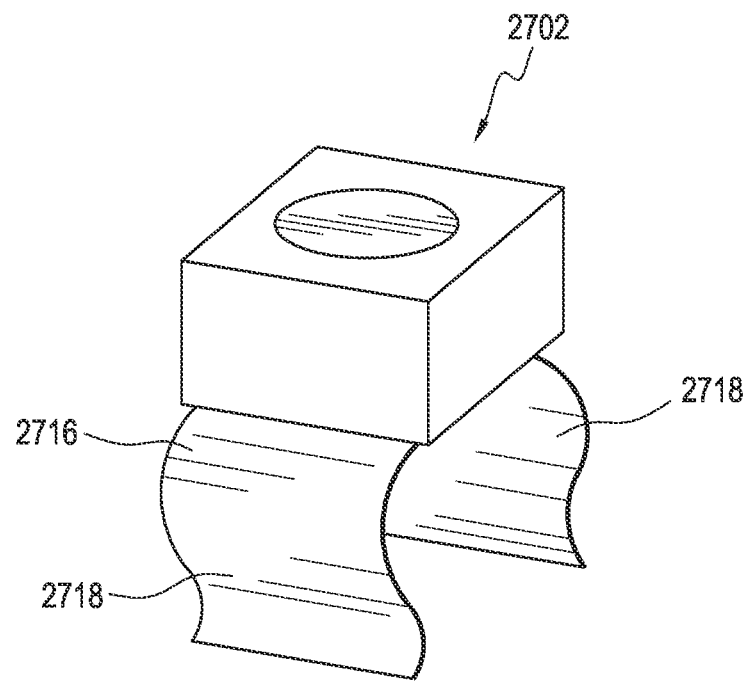
FIG. 48 shows a perspective view of disinfecting cap in accordance with embodiments of the invention.
Figure 49:
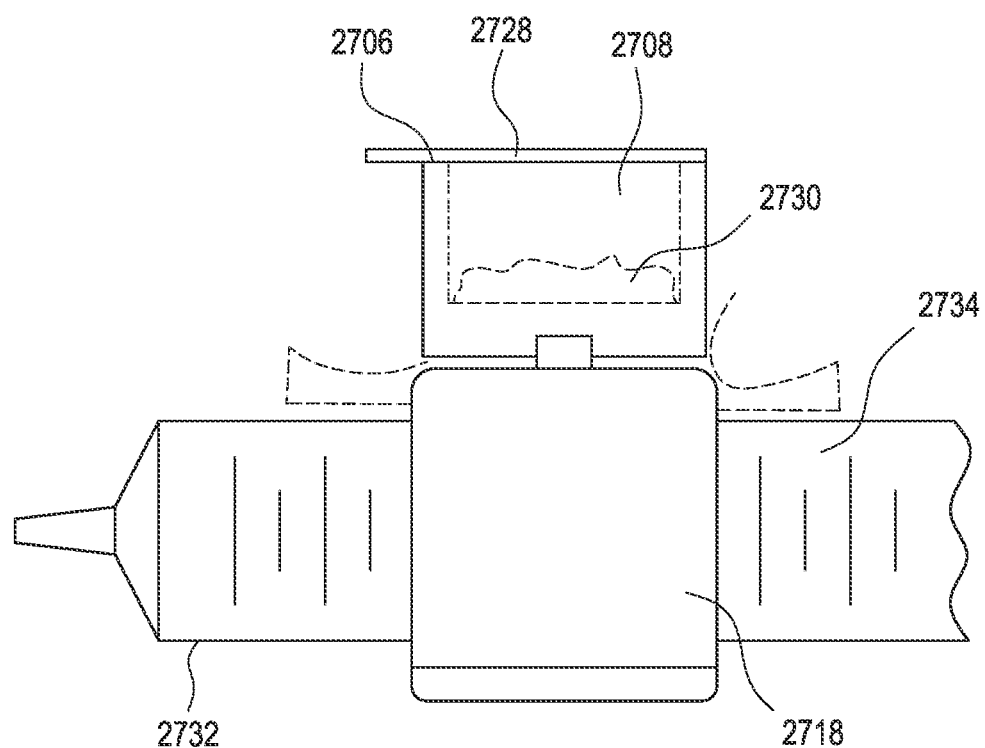
FIG. 49 shows a side view of the disinfecting cap of FIG. 48.
Figure 50:
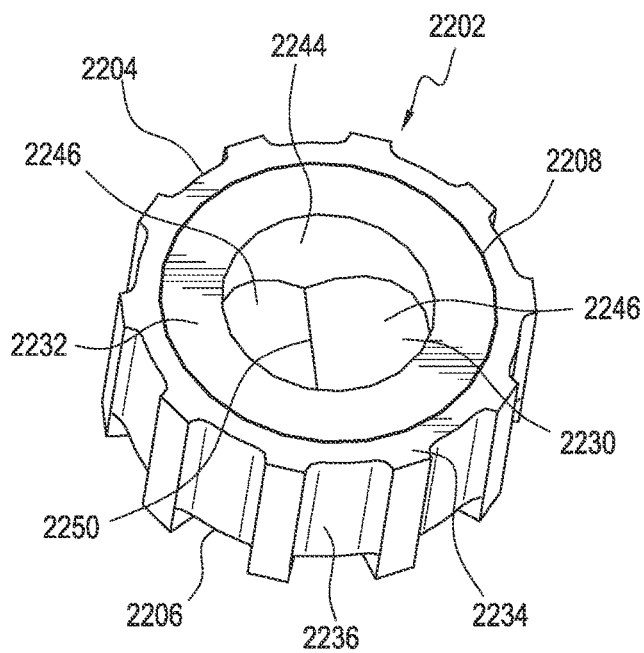
FIG. 50 shows a perspective view of disinfecting cap in accordance with embodiments of the invention.
Figure 51:
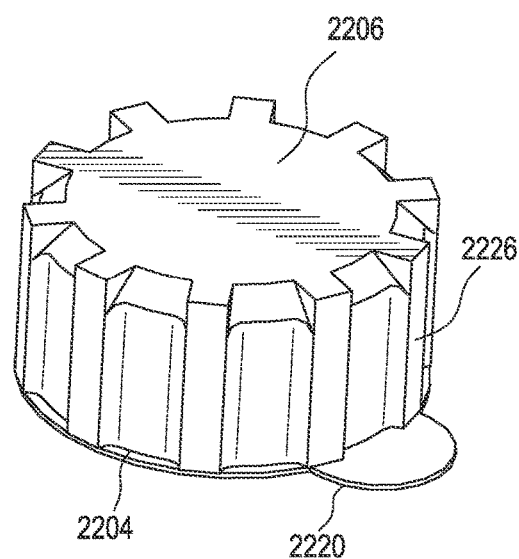
FIG. 51 shows a second perspective view of the disinfecting cap of FIG. 50.
Figure 52:
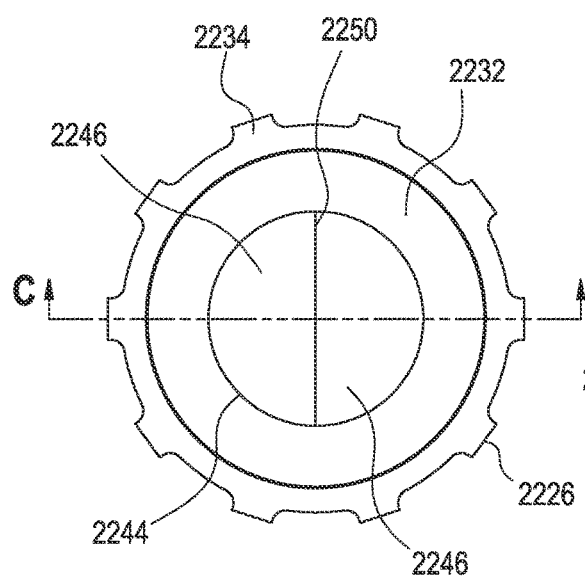
FIG. 52 shows a view of the proximal end of the cap of FIG. 50.
Figure 53:
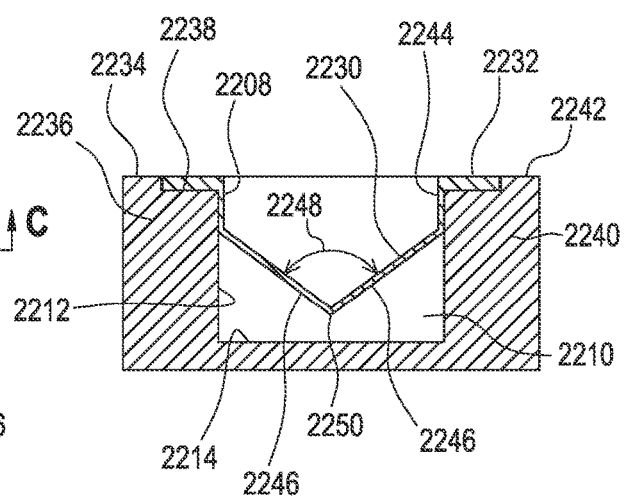
FIG. 53 shows a cross-sectional view along line C-C of the disinfecting cap of FIG. 50.
Figure 54:
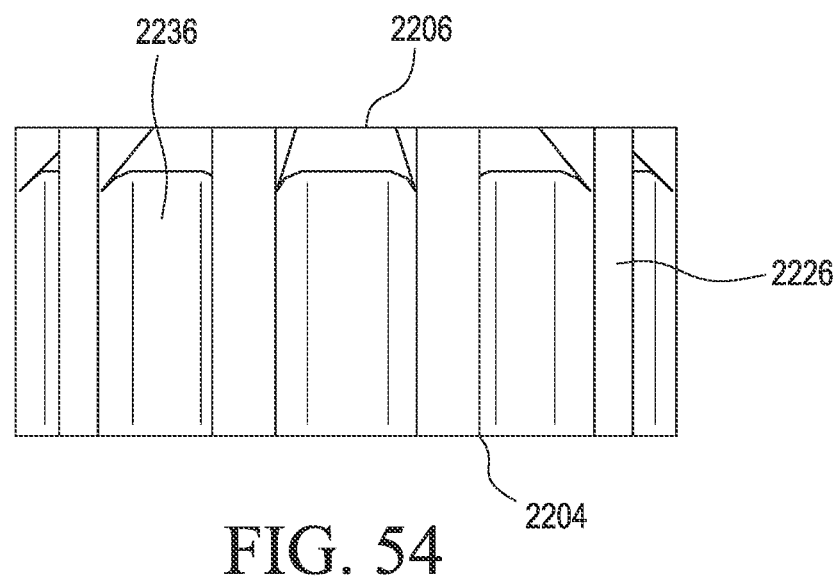
FIG. 54 shows a side view of the cap of FIG. 50.

In an alternative embodiment, as illustrated in FIGS. 48-49, the cap 2702 may include a clip 2716. The clip may include resilient arms 2718 that are sized to releasably engage the barrel 2734 of a syringe 2732.

An absorbent material 2730 may be positioned inside the cavity 2408. The absorbent material may be infused with a disinfecting solution. Alternatively, the disinfecting solution may be present in the cavity without the use of an absorbent material. The cap 2702 may include a peelable lid 2728 that is sealed to the top surface 2706 of the cap in order to retain the disinfecting solution within the cap cavity 2708, thereby preventing the disinfecting solution from leaking or evaporating out from the cap 2702.

FIGS. 50-53 show an illustrative disinfecting cap in accordance with embodiments of the invention. The cap 2202 is molded from PU and may be reaction injection molded from PU foam into the final shape. The molded foam 2240 may include a skin 2242 that is resistant to IPA or other disinfecting solutions. The cap includes an open proximal end 2204 and a closed distal end 2206. The cap 2202 may include ribs 2226 formed on an exterior surface to provide easier handling and twisting of the cap by a healthcare worker. The ribs may extend parallel to a central axis of the cap, as illustrated, or may have another configuration. Alternatively, other knurling, texturing, finger shaped or grip elements may be provided.

The proximal end has an opening 2208 that provides access to a cavity 2210. The cavity 2210 has a generally cylindrical sidewall 2212 and distal or bottom surface 2214. The cylindrical sidewall 2212 may have a constant diameter along a longitudinal axis of the cap or the diameter may increase along the longitudinal axis such that the diameter of the sidewall is greater at the distal end than the diameter of the sidewall at the proximal end at or near the bottom surface 2214 in one embodiment. In another embodiment the diameter may decrease along the longitudinal axis such that the diameter of the sidewall is smaller at the distal end than the diameter of the sidewall at the proximal end at or near the bottom surface 2214.

Embodiments of the cap may include a valve 2230. The valve may be a "duckbill," diaphragm or other type of self-sealing valve. As shown in the illustrative embodiment, the valve 2230 includes a lip 2232 that extends over a top surface 2234 of the cavity sidewall 2236. The sidewall 2236 may include a counterbore 2238 or recess to accommodate the lip 2232 such that a proximal surface of the lip is flush with a proximal surface of the cap. A portion 2244 of the valve 2230 extends distally from the lip 2232 along the inside diameter 2212 of the cavity 2210. Starting at a position below the proximal surface of the cap, two generally planar portions 2246 of the valve extend distally at a relative angle so as to meet at an acute angle 2248. A slit 2250 is formed at the intersection of the two planar portions 2246.

When a healthcare worker inserts the port to be cleaned into the cap, the end of the port enters through the valve and is exposed to the disinfecting solution. The valve secures the end of the port in the cavity once the port passes through the slit 2250. A portion of the cavity 2210 may be filled with IPA or another disinfecting substance in liquid or gel form. Alternatively, at least a portion of the cavity may be filled with a foam, such as an open cell PU foam. The foam may be infused with a disinfecting substance. The valve may operate to secure the cap to the port and may also prevent or reduce leaking of disinfecting solution out of the cap.

The cap 2202 may include a peelable lid 2220 that is sealed to the skin 1742 of the cap in order to retain the disinfecting solution within the cap cavity 2210, thereby preventing the disinfecting solution from leaking or evaporating out from the cap 2202.

Figure 55:
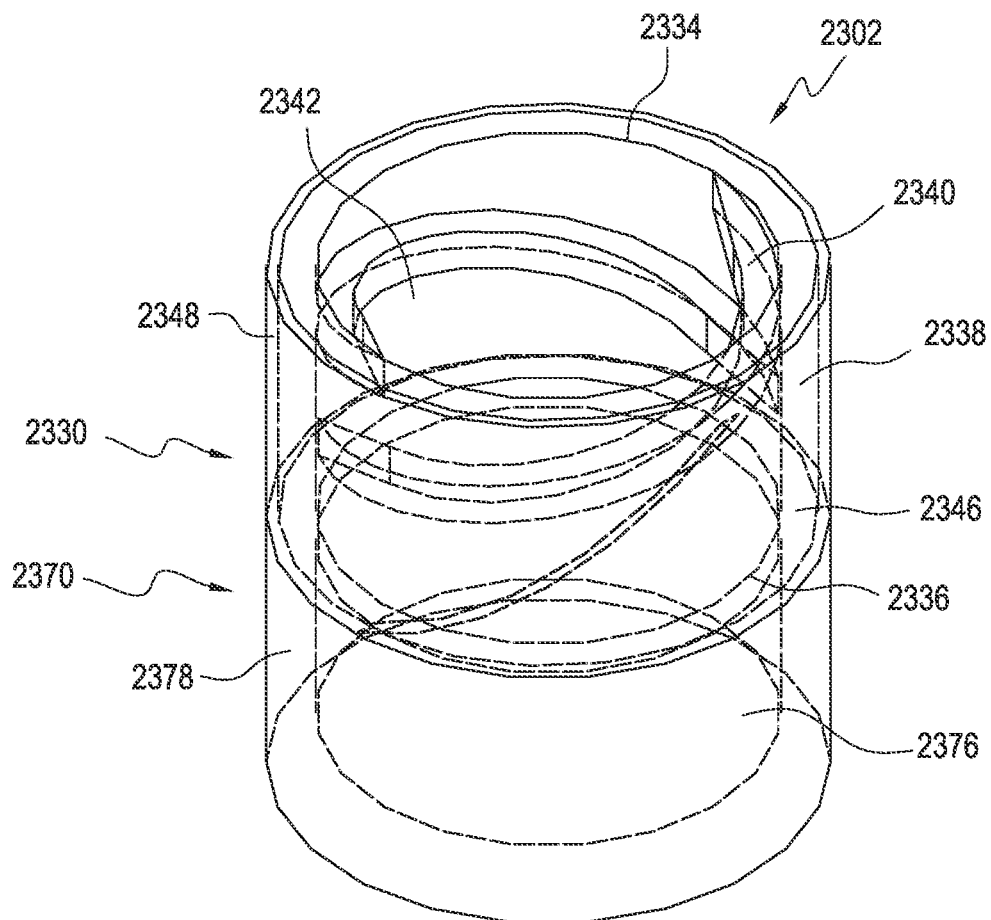
FIG. 55 shows a perspective view of disinfecting cap in accordance with embodiments of the invention.
Figure 56:
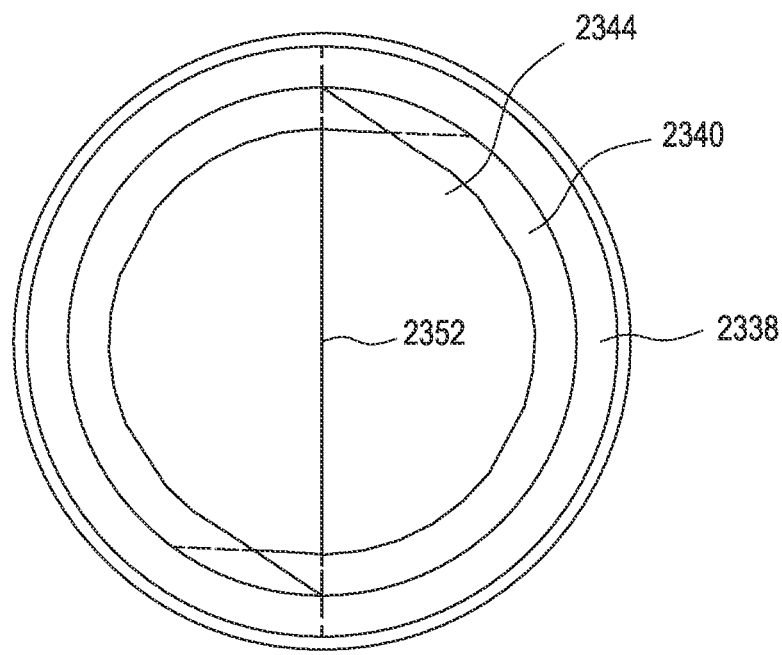
FIG. 56 shows a view of the proximal end of the cap of FIG. 55.
Figure 57:
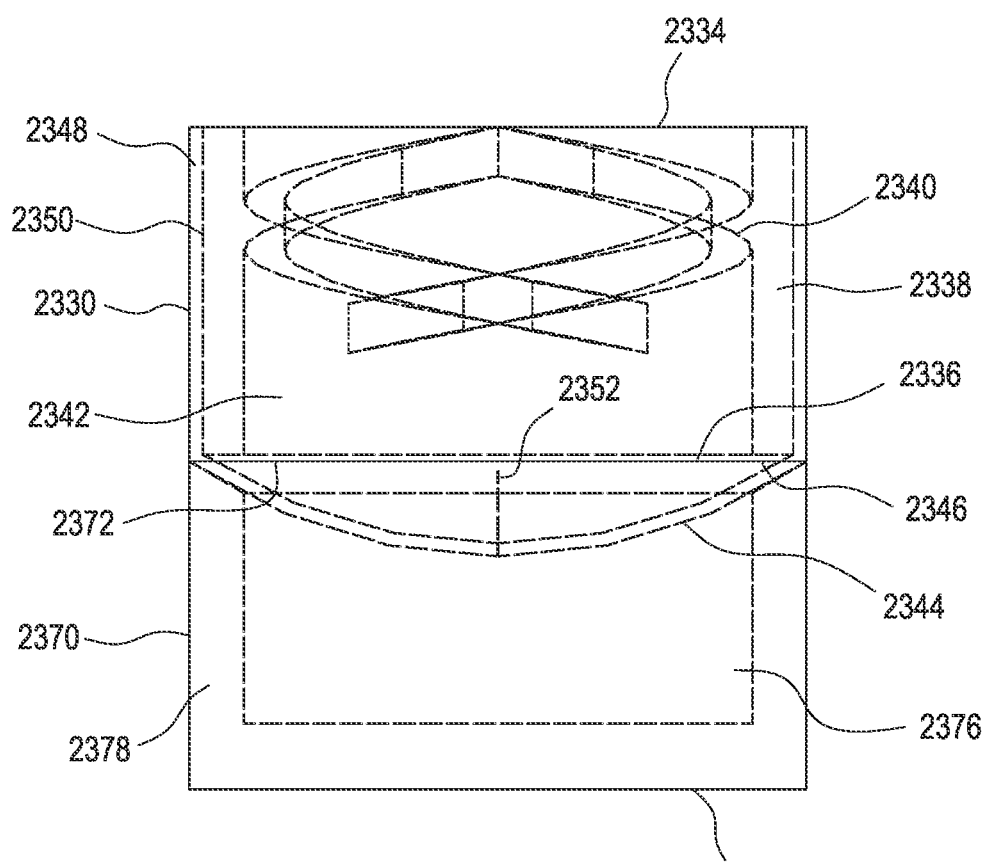
FIG. 57 shows an end view of the cap of FIG. 55.

FIGS. 55-57 show an illustrative disinfecting cap in accordance with embodiments of the invention. The cap 2302 includes a first engaging portion 2330 and a second reservoir portion 2370. The engaging portion 2330 includes side a generally cylindrical sidewall 2338. The engaging portion includes an open proximal end 2334 and an open distal end 2336 and encompasses a cavity 2342. Threads 2340 may be formed on the sidewall in order to engage with the threads of a site to be cleaned and to retain the cap on the site. The cylindrical sidewall may have a constant diameter along a longitudinal axis of the cap or the diameter may increase along the longitudinal axis such that the diameter of the sidewall is greater at the proximal end 2334 than the diameter of the sidewall at the distal end 2336. In another embodiment the diameter may decrease along the longitudinal axis such that the diameter of the sidewall is smaller at the proximal end 2334 than the diameter of the sidewall at the distal end 2336.

The cap 2302 may include ribs (not shown) formed on an exterior surface to provide easier handling and twisting of the cap by a healthcare worker. The ribs may extend parallel to a central axis of the cap, as illustrated, or may have another configuration. Alternatively, other knurling, texturing, finger shaped or grip elements may be provided.

The engaging portion 2330 includes a diaphragm valve 2344 that covers the distal end 2336 of the cavity 2342. The valve may cover a distal end 2346 of sidewall 2338 as well as the open end 2336 of the cavity 2342. A portion 2348 of the diaphragm valve 2344 may extend beyond the opening along an outside surface 2350 of sidewall 2338. The valve may be molded over the sides and open end of the engaging portion. The diaphragm valve 2344 includes a slit 2352. A female port or other access site is pushed through the slit 2350 into the cavity 2342 as the threads 2340 of the cavity engage the threads of the port. Alternatively, the diaphragm valve may secure the end of the port in the cavity once the port passes through the slit.

The cap 2302 further includes a reservoir portion 2370. The reservoir portion has an open proximal end 2372 and a closed distal end 2374. A generally cylindrical sidewall 2378 encompasses a cavity 2376. The reservoir portion may be sonically welded or otherwise attached to the engaging portion. A portion of the cavity 2376 may be filled with IPA or another disinfecting substance in liquid or gel form. Alternatively, at least a portion of the cavity may be filled with a foam, such as an open cell PU foam. The foam may be infused with a disinfecting substance. Accordingly, as a female port or other access site is pushed through the slit 2352 of the engaging portion 2330 into the cavity 2376 of the reservoir portion 2370, the port is exposed to the disinfecting substance.

Figure 58:
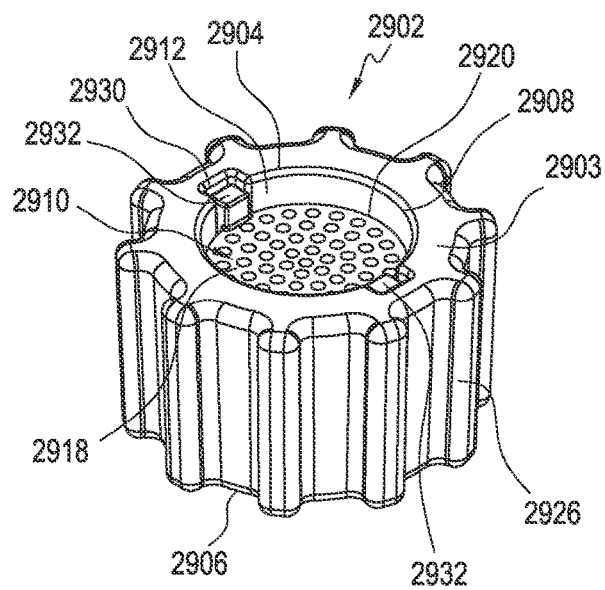
FIG. 58 shows a perspective view of disinfecting cap in accordance with embodiments of the invention.
Figure 59:
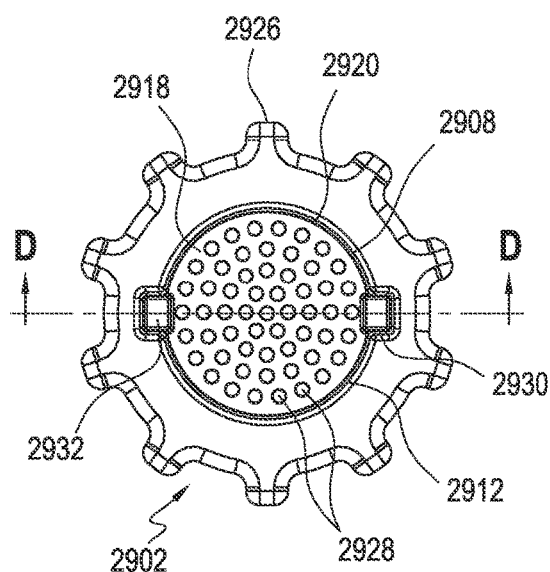
FIG. 59 shows a view of the proximal end of the cap of FIG. 58.
Figure 60:
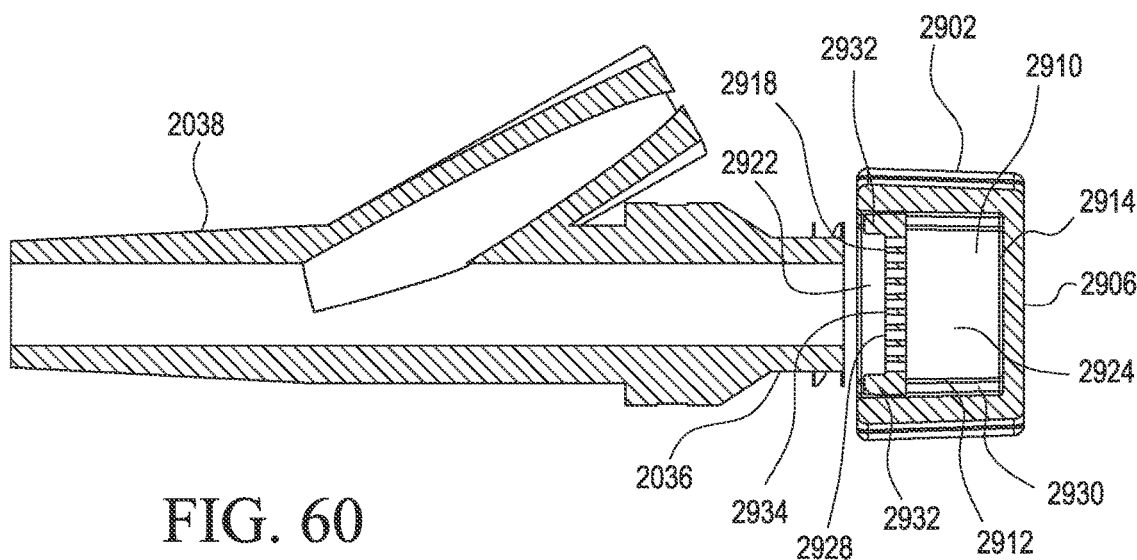
FIG. 60 shows a cross-sectional view along line D-D of the disinfecting cap of FIG. 58 along with a cross-sectional view of a Y-site having a threaded female port.

FIGS. 58-60 show an illustrative disinfecting cap in accordance with embodiments of the invention. The cap 2902 may be molded from PP. Alternatively, the cap may be molded from PU and may be reaction injection molded from PU foam into the final shape. The molded foam may include a skin that is resistant to IPA or other disinfecting solutions. The cap 2902 includes an open proximal end 2904 and a closed distal end 2906. The cap may include ribs 2926 formed on an exterior surface to provide easier handling and twisting of the cap by a healthcare worker. The ribs may extend parallel to a central axis of the cap, as illustrated, or may have another configuration. Alternatively, other knurling, texturing, finger shaped or grip elements may be provided.

The proximal end has an opening 2908 that provides access to a cavity 2910. The cavity 2910 has a generally cylindrical sidewall 2912 and distal or bottom surface 2914. Threads may be formed on the sidewall in order to engage with the threads of a site to be cleaned and to retain the cap on the site. The cylindrical sidewall may have a constant diameter along a longitudinal axis of the cap or the diameter may increase along the longitudinal axis such that the diameter of the sidewall is greater at the proximal end than the diameter of the sidewall at the distal end at or near the bottom surface 2914 in one embodiment. In another embodiment the diameter may decrease along the longitudinal axis such that the diameter of the sidewall is smaller at the distal end than the diameter of the sidewall at the proximal end at or near the bottom surface 2914.

The cap 2902 may also include a separating disc or screen 2918. The illustrative screen 2918 has a generally cylindrical disc/flat circular shape with an outside diameter 2920 that corresponds across at least part of its perimeter to the sidewall 2912 of the cavity 2910. The screen 2918 divides the cavity 2910 into two portions, a proximal portion 2922 adjacent to the opening 2908 and a distal portion 2924 adjacent to the bottom surface 2914 of the cavity. The distal cavity 2924 may be filled at least partially with a disinfecting solution.

The screen 2918 may have one or more through holes 2928. The holes 2928 may be generally cylindrical in shape and may be arranged in any appropriate pattern. Alternatively, the holes may be formed in other shapes. The holes may be formed with a constant cross-section as illustrated in FIGS. 58-60, or the holes may have a different cross-section. For example, the holes may have a conical or pyramid shape.

The sidewall 2912 of the cavity 2910 may include one or more slots 2930. The slots extend parallel to a longitudinal axis of the cap. Ridges or arms 2932 extend from the outside diameter 2920 of the screen 2918. These arms 2932 engage with the slots 2930 in the cavity diameter and allow the screen 2918 to slide longitudinally within the cavity 2910. The arms 2932 may extend longitudinally above a top surface 2934 of the screen 2918.

FIGS. 58 and 60 show the cap prior to insertion of the female port 2036 of the Y-site 2038 into the cap. The screen is positioned adjacent the open end 2904 of the cap such that the arms 2932 are parallel with or below the top surface 2903 of the cap.

Figure 61:
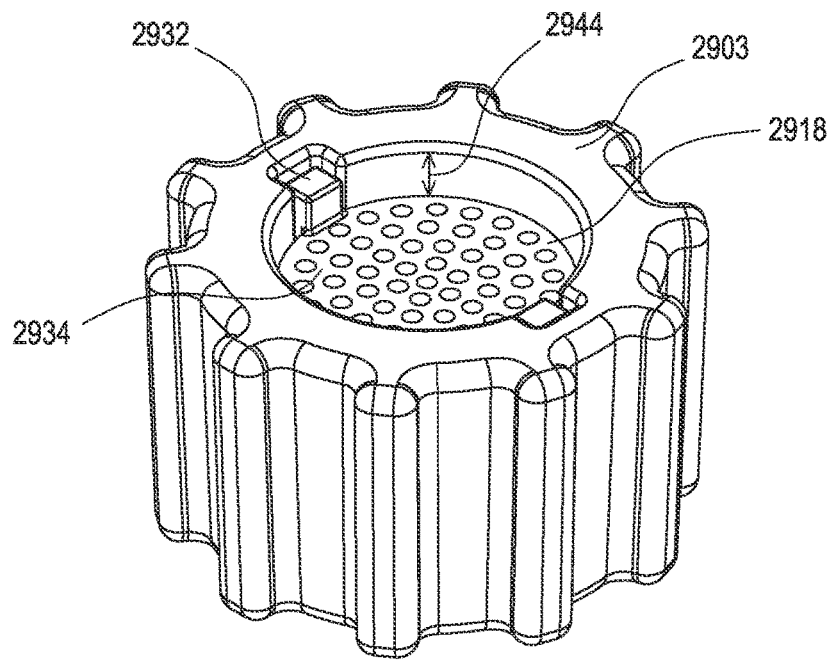
FIG. 61 shows a perspective view of disinfecting cap in accordance with embodiments of the cap shown in FIG. 58 at a subsequent stage of use.
Figure 62:
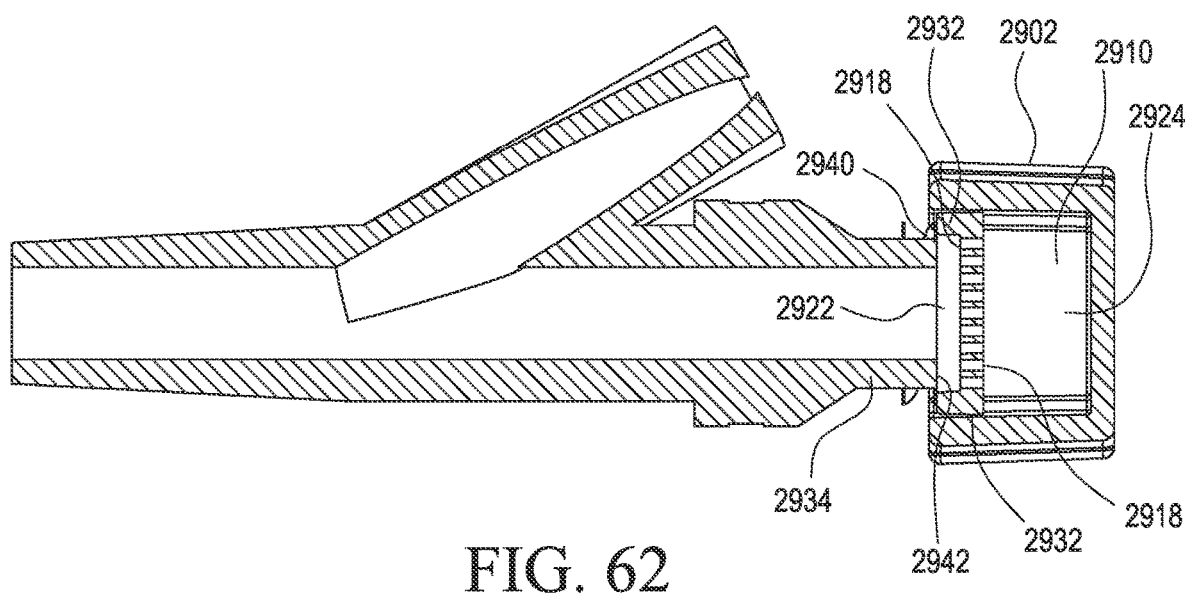
FIG. 62 shows a cross-sectional view along line D-D of the disinfecting cap of FIG. 61 along with a cross-sectional view of a Y-site having a threaded female port.

FIGS. 61-62 show the cap 2902 at the point that the female port 2934 first makes contact with the cap. In the illustrative embodiment, threads 2940 formed on an outside diameter of the female port or the distal surface 2942 of the port 2934 contact the arms 2932 of the screen 2918. The screen top surface 2934 is spaced apart from the top surface 2903 of the cap by a first distance 2944. At this point, the distal portion 2924 of the cavity 2910 is at least partially filled with a disinfecting solution while the proximal portion 2922 of the cavity does not include any disinfecting solution.

Figure 63:
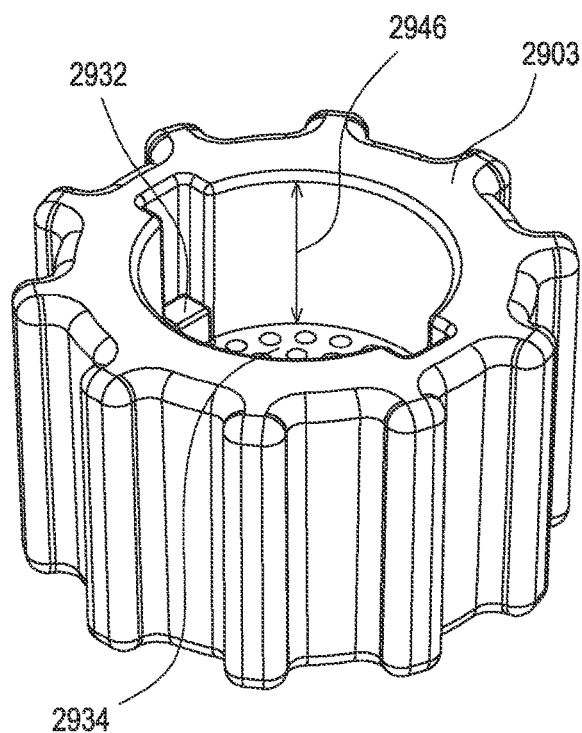
FIG. 63 shows a perspective view of disinfecting cap in accordance with embodiments of the cap shown in FIG. 61 at a subsequent stage of use.
Figure 64:
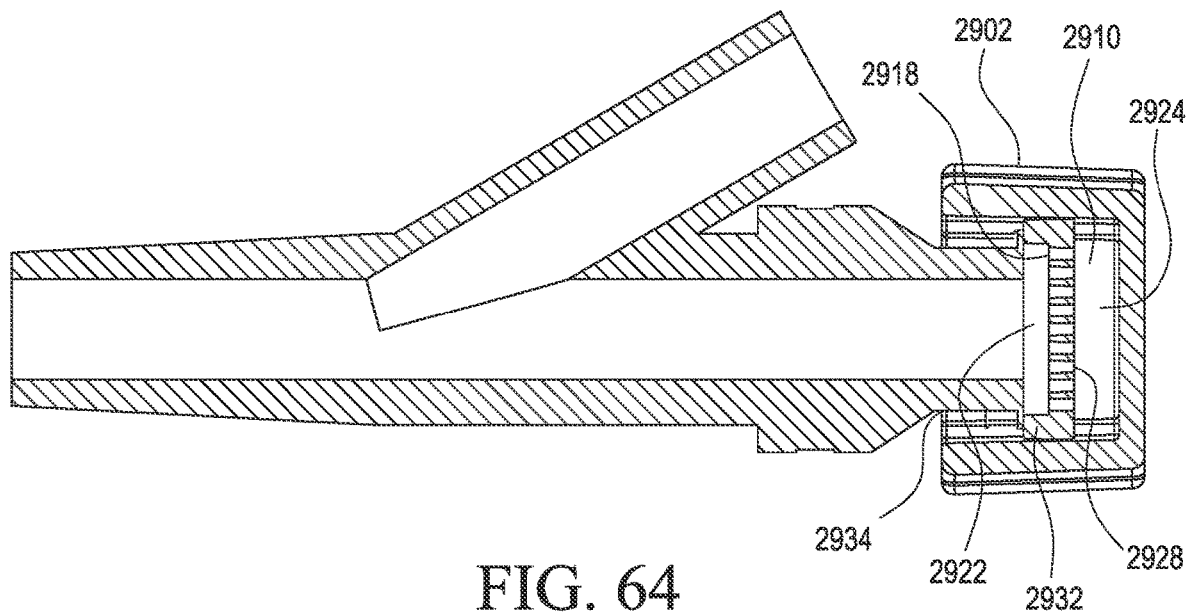
FIG. 64 shows a cross-sectional view along line D-D of the disinfecting cap of FIG. 63 along with a cross-sectional view of a Y-site having a threaded female port.

FIGS. 63-64 show the cap 2902 at a point that the female port 2934 has been pushed partially within the cap. The screen top surface 2934 is spaced apart from the top surface 2903 of the cap by a second, greater distance 2946. At this point, the distal portion 2924 of the cavity 2910 remains at least partially filled with a disinfecting solution, but at least a portion of the disinfecting solution has been forced through the holes 2928 into the proximal portion 2922 of the cavity. The disinfecting solution wets and disinfects the surface of the female port 2934.

Figure 65:
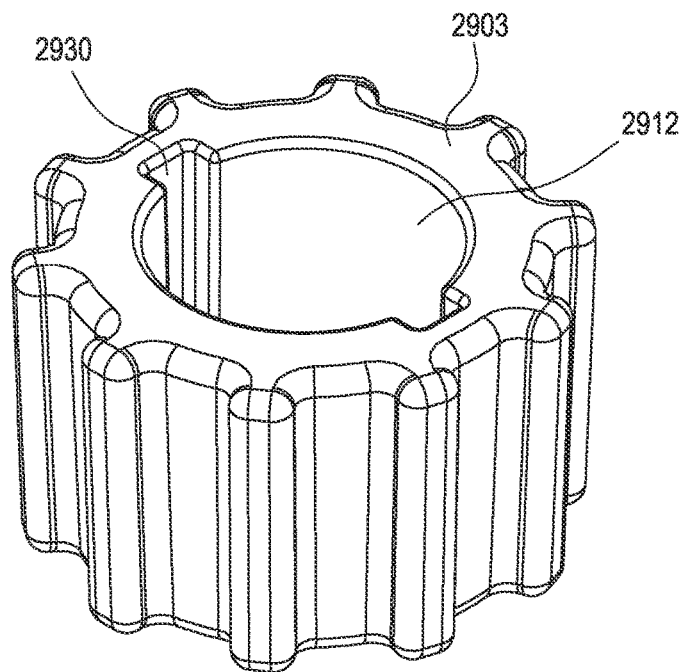
FIG. 65 shows a perspective view of disinfecting cap in accordance with embodiments of the cap shown in FIG. 63 at a subsequent stage of use.
Figure 66:
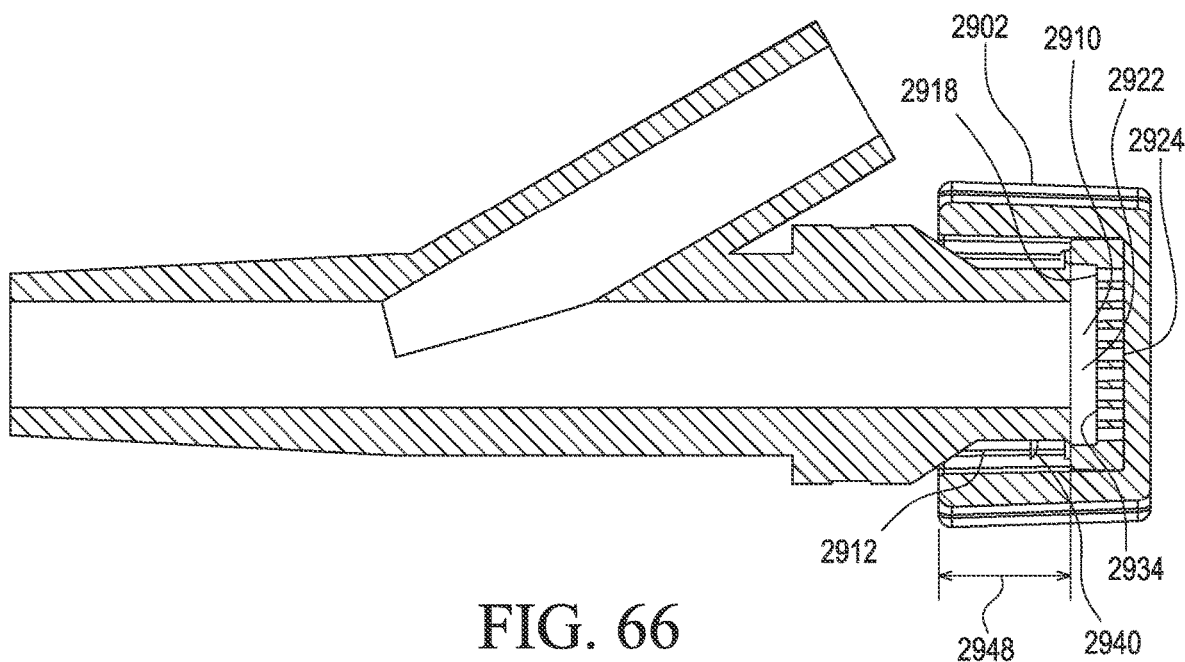
FIG. 66 shows a cross-sectional view along line D-D of the disinfecting cap of FIG. 67 along with a cross-sectional view of a Y-site having a threaded female port.

FIGS. 65-66 show the cap 2902 at a point that the female port 2934 has been fully pushed into the cap. The screen top surface 2934 is spaced apart from the top surface 2903 of the cap by a third, greater distance 2948. At this point, the distal portion 2924 of the cavity 2910 may be completely collapsed as shown in the illustrative embodiment. Alternatively, the distal portion of the cavity may retain some volume that is at least partially filled with a disinfecting solution but with a significant portion of the disinfecting solution having been forced through the holes 2928 into the proximal portion 2922 of the cavity. The inside diameter 2912 of the cavity 2910 may engage the threads 2940 of the female port 2934 with a friction fit in order to retain the cap on the port.

As the port 2934 is inserted into the cap, it forces the screen 2918 into the distal cavity portion 2924, and disinfecting solution is forced through holes 2918 into the proximal cavity portion 2922 where it wets and disinfects the port. The disinfecting fluid may flow through the holes such that it flows along the sidewall 2912 of the cavity and onto the port. Alternatively, the speed of inserting the port may be such that the disinfecting fluid is forced through the holes 2918 with sufficient force to cause the disinfecting fluid to spray onto and coat the port surface.

The embodiments shown in FIGS. 58-66 provide examples in which the screen 2918 has a certain thickness between the top surface 2934 and a bottom surface. In alternative embodiments of the invention, the screen may have a different thickness that is thinner or thicker than the exemplary embodiment shown. In view of the disclosure of this application, one of ordinary skill in the art would understand that the thickness of the screen in combination with the size and shape of the holes 2928 would affect the disinfecting fluid flows or sprays onto the port surface.

The cap 2902 may include a peelable lid that is sealed to a top surface 2903 of the cap in order to retain the disinfecting solution within the cap cavity 2910, thereby preventing the disinfecting solution from leaking or evaporating out from the cap 2902.

Although a few embodiments have been described in detail above, other modifications are possible. For instance, any of the embodiments described above may be sized and scaled for a particular medical implement, such as a stethoscope or otoscope. Other embodiments may be within the scope of the following claims.

This application provides a description of various implementations and embodiments of a device for cleaning medical implements. The various embodiments have been described as having a variety of features. It will be understood by one of ordinary skill in the art that features of the various embodiments are intended to be interchangeable, and features described in the context of one embodiment may be implemented in conjunction with a device having the features and structure of another embodiment.

What is claimed is:

1. A disinfecting cap comprising:
    a housing comprising:
        a bottom wall, and
        a sidewall extending from the bottom wall, the sidewall surrounding an interior chamber and an opening into the interior chamber, the sidewall comprising a non-threaded interior surface extending from the bottom wall, along the sidewall, and to the opening, the interior surface comprising a deformable portion being configured to securely attach to a thread of a medical device;
    a cleaning material being configured to releasably retain an antiseptic liquid, the cleaning material being positioned in the interior chamber and being separate from the deformable portion of the interior surface;
    a seal being removably attached to an outer surface of the housing and extending over the interior chamber such that the cleaning material is exposed upon removal of the seal; and
    a resilient retention element positioned on an interior surface of the sidewall;
    wherein as the cap is attached to a port of the medical device, a thread of the port pushes past at least a portion of the retention element, and the element rebounds into a position in which the retention element engages the thread.

2. The disinfecting cap of claim 1 further comprising packaging that surrounds at least a portion of the housing.

3. The disinfecting cap of claim 1, wherein the interior surface engages the thread of the medical device with a friction fit.

4. The disinfecting cap of claim 1 wherein the seal comprises a peelable lid.

5. The disinfecting cap of claim 1 wherein the cleaning material comprises an absorbent material positioned within the chamber.

6. The disinfecting cap of claim 5 wherein the antiseptic liquid comprises a disinfecting solution infused into the absorbent material.

7. The disinfecting cap of claim 4, wherein the peelable lid seals the chamber and retains the disinfecting solution.

8. The disinfecting cap of claim 1, wherein the retention element extends from the interior surface of the sidewall.

9. The disinfecting cap of claim 1, wherein the retention element operates as a valve.

10. The disinfecting cap of claim 6, wherein the retention element reduces leaking of disinfecting solution out of the cap.

11. The disinfecting cap of claim 1, wherein the retention element securely attaches to the thread of the medical device as the disinfecting cap is applied to the port in a direction along a longitudinal axis of the disinfecting cap.

12. The disinfecting cap of claim 1, wherein the retention element securely attaches to the thread of the port without requiring rotation of the disinfecting cap or the medical device.

13. The disinfecting cap of claim 1 further comprising one or more ribs, wherein each of the one or more ribs extends at least partially along an external surface of the sidewall.

14. The disinfecting cap of claim 1 wherein the chamber comprises a counterbore.

15. The disinfecting cap of claim 1, wherein the deformable portion of the interior surface is configured to securely attach to the thread of the medical device as the sanitizing cap is applied to the medical device in a direction along a longitudinal axis of the disinfecting cap.

16. The disinfecting cap of claim 15, wherein the deformable portion of the interior surface is configured to securely attach to the thread of the medical device without requiring rotation of the disinfecting cap or the medical device.

17. The disinfecting cap of claim 1, wherein the deformable portion of the interior surface does not comprise a screw thread.

* * * * *